US011759605B2

(12) United States Patent
Romo et al.

(10) Patent No.: US 11,759,605 B2
(45) Date of Patent: Sep. 19, 2023

(54) TOOL AND METHOD FOR USING SURGICAL ENDOSCOPE WITH SPIRAL LUMENS

(71) Applicant: Auris Health, Inc., Redwood City, CA (US)

(72) Inventors: Enrique Romo, Dublin, CA (US); Leo Centeno, East Palo Alto, CA (US)

(73) Assignee: Auris Health, Inc., Redwood City, CA (US)

( * ) Notice: Subject to any disclaimer, the term of this patent is extended or adjusted under 35 U.S.C. 154(b) by 418 days.

(21) Appl. No.: 17/015,514

(22) Filed: Sep. 9, 2020

(65) Prior Publication Data

US 2020/0406002 A1 Dec. 31, 2020

Related U.S. Application Data

(62) Division of application No. 14/583,021, filed on Dec. 24, 2014, now Pat. No. 10,792,464.

(Continued)

(51) Int. Cl.
*A61M 25/00* (2006.01)
*A61B 1/00* (2006.01)
(Continued)

(52) U.S. Cl.
CPC ......... *A61M 25/005* (2013.01); *A61B 1/0057* (2013.01); *A61B 1/0058* (2013.01);
(Continued)

(58) Field of Classification Search
CPC ......... A61B 2017/320084; A61M 2025/0057; A61M 25/007
(Continued)

(56) References Cited

U.S. PATENT DOCUMENTS 3,572,325 A 3/1971 Bazell et al.
3,595,074 A 7/1971 Johnson
(Continued)

FOREIGN PATENT DOCUMENTS

CN 1364275 8/2002
CN 1846181 10/2006
(Continued)

OTHER PUBLICATIONS

Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
(Continued)

*Primary Examiner* — Phillip A Gray
(74) *Attorney, Agent, or Firm* — Chang & Hale LLP

(57) ABSTRACT

An embodiment of the present invention provides for an elongated medical device with a hypotube backbone running through the device, and a spiral lumen spiraled around the backbone along the length of the backbone. The backbone may be formed from a nitinol alloy for increased bendability without compromising axial stiffness. The device may also incorporate a jacket around the hypotube and spiral lumen formed using either melting, molding, bonding, or casting. The spiral lumen may be configured to accommodate a variety of uses, including actuation members (e.g., pull wires), tools, and means for aspiration, irrigation, image capture, and illumination. Additionally, the present invention provides a method for constructing an elongated medical device with a hypotube backbone running through the device, and a spiral lumen spiraled around the backbone along the length of the backbone.

19 Claims, 41 Drawing Sheets

Related U.S. Application Data

(60) Provisional application No. 62/057,936, filed on Sep. 30, 2014, provisional application No. 62/019,816, filed on Jul. 1, 2014.

(51) Int. Cl.
*A61B 1/005* (2006.01)
*A61B 34/30* (2016.01)
*A61M 25/01* (2006.01)

(52) U.S. Cl.
CPC .......... *A61B 1/00149* (2013.01); *A61B 34/30* (2016.02); *A61M 25/0012* (2013.01); *A61B 2034/301* (2016.02); *A61M 25/0023* (2013.01); *A61M 25/0043* (2013.01); *A61M 25/0053* (2013.01); *A61M 25/0147* (2013.01); *A61M 2025/0059* (2013.01)

(58) Field of Classification Search
USPC ........................................ 604/526, 22, 95.04
See application file for complete search history.

(56) References Cited

U.S. PATENT DOCUMENTS

| | | |
|---|---|---|
| 3,913,565 A | 10/1975 | Kawahara |
| 4,294,234 A | 10/1981 | Matsuo |
| 4,384,493 A | 5/1983 | Grunbaum |
| 4,392,485 A | 7/1983 | Hiltebrandt |
| 4,597,388 A | 7/1986 | Koziol et al. |
| 4,607,619 A | 8/1986 | Seike et al. |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro |
| 4,846,791 A | 7/1989 | Hattler et al. |
| 4,869,238 A | 9/1989 | Opie et al. |
| 4,905,673 A | 3/1990 | Pimiskern |
| 4,906,496 A | 3/1990 | Hosono et al. |
| 4,907,168 A | 3/1990 | Boggs |
| 4,967,732 A | 11/1990 | Inoue |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,217,002 A | 6/1993 | Katsurada |
| 5,234,428 A | 8/1993 | Kaufman |
| 5,251,611 A | 10/1993 | Zehel et al. |
| 5,257,617 A | 11/1993 | Takahashi |
| 5,261,391 A | 11/1993 | Inoue |
| 5,287,861 A | 2/1994 | Wilk |
| 5,313,934 A | 5/1994 | Wiita et al. |
| 5,386,818 A | 2/1995 | Schneebaum |
| 5,425,735 A | 6/1995 | Rosen et al. |
| 5,426,687 A | 6/1995 | Goodall et al. |
| 5,448,988 A | 9/1995 | Watanabe |
| 5,472,406 A | 12/1995 | De La Torre et al. |
| 5,478,330 A | 12/1995 | Imran et al. |
| 5,482,029 A | 1/1996 | Sekiguchi |
| 5,489,270 A | 2/1996 | van Erp |
| 5,507,725 A * | 4/1996 | Savage ............. A61M 25/0144 604/95.04 |
| 5,533,985 A | 7/1996 | Wang |
| 5,559,294 A | 9/1996 | Hoium et al. |
| 5,572,999 A | 11/1996 | Funda et al. |
| 5,580,200 A | 12/1996 | Fullerton |
| 5,662,590 A | 9/1997 | De La Torre et al. |
| 5,681,296 A | 10/1997 | Ishida |
| 5,695,500 A | 12/1997 | Taylor et al. |
| 5,704,534 A | 1/1998 | Huitema et al. |
| 5,720,775 A | 2/1998 | Lamard |
| 5,741,429 A | 4/1998 | Donadio, III |
| 5,749,889 A | 5/1998 | Bacich et al. |
| 5,792,135 A | 8/1998 | Madhani et al. |
| 5,855,583 A | 1/1999 | Wang et al. |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,910,129 A | 6/1999 | Koblish et al. |
| 5,938,586 A | 8/1999 | Wilk |
| 5,938,587 A | 8/1999 | Taylor et al. |
| 6,012,494 A | 1/2000 | Balazs |
| 6,033,371 A | 3/2000 | Torre et al. |
| 6,143,013 A | 11/2000 | Samson et al. |
| 6,157,853 A | 12/2000 | Blume et al. |
| 6,174,280 B1 | 1/2001 | Oneda |
| 6,197,015 B1 | 3/2001 | Wilson |
| 6,198,974 B1 | 3/2001 | Webster, Jr. |
| 6,234,958 B1 | 5/2001 | Snoke et al. |
| 6,315,715 B1 | 11/2001 | Taylor et al. |
| 6,326,616 B1 | 12/2001 | Andrien et al. |
| 6,398,792 B1 | 6/2002 | O'Connor |
| 6,404,497 B1 | 6/2002 | Backman |
| 6,406,486 B1 | 6/2002 | De La Torre et al. |
| 6,436,107 B1 | 8/2002 | Wang et al. |
| 6,464,632 B1 | 10/2002 | Taylor |
| 6,485,411 B1 | 11/2002 | Konstorum |
| 6,491,626 B1 | 12/2002 | Stone et al. |
| 6,537,205 B1 | 3/2003 | Smith |
| 6,554,793 B1 | 4/2003 | Pauker et al. |
| 6,638,246 B1 | 10/2003 | Naimark et al. |
| 6,671,581 B2 | 12/2003 | Niemeyer et al. |
| 6,716,178 B1 | 4/2004 | Kilpatrick et al. |
| 6,736,784 B1 | 5/2004 | Menne et al. |
| 6,746,422 B1 | 6/2004 | Noriega |
| 6,749,560 B1 | 6/2004 | Konstorum |
| 6,763,259 B1 | 7/2004 | Hauger et al. |
| 6,790,173 B2 | 9/2004 | Saadat |
| 6,827,710 B1 | 12/2004 | Mooney et al. |
| 6,827,712 B2 | 12/2004 | Tovey et al. |
| 6,837,846 B2 | 1/2005 | Jaffe |
| 6,908,428 B2 | 6/2005 | Aizenfeld |
| 6,921,362 B2 | 7/2005 | Ouchi |
| 6,958,035 B2 | 10/2005 | Friedman et al. |
| 7,008,401 B2 | 3/2006 | Thompson et al. |
| 7,087,061 B2 | 8/2006 | Chernenko et al. |
| 7,130,700 B2 | 10/2006 | Gardeski et al. |
| 7,344,528 B1 | 3/2008 | Tu et al. |
| 7,351,193 B2 | 4/2008 | Forman et al. |
| 7,594,903 B2 | 9/2009 | Webler et al. |
| 7,645,230 B2 | 1/2010 | Mikkaichi |
| 7,645,231 B2 | 1/2010 | Akiba |
| 7,725,214 B2 | 5/2010 | Diolaiti |
| 7,789,827 B2 | 9/2010 | Landry |
| 7,883,475 B2 | 2/2011 | Dupont et al. |
| 7,930,065 B2 | 4/2011 | Larkin et al. |
| 7,967,799 B2 | 6/2011 | Boukhny |
| 8,046,049 B2 | 10/2011 | Govari et al. |
| 8,049,873 B2 | 11/2011 | Hauger et al. |
| 8,052,636 B2 | 11/2011 | Moll et al. |
| 8,224,484 B2 | 7/2012 | Swarup et al. |
| 8,246,536 B2 | 8/2012 | Ochi |
| 8,414,564 B2 | 4/2013 | Goldshleger et al. |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,518,024 B2 | 8/2013 | Williams et al. |
| 8,602,031 B2 | 12/2013 | Reis et al. |
| 8,652,030 B2 | 2/2014 | Matsuura et al. |
| 8,686,747 B2 | 4/2014 | Berner |
| 8,720,448 B2 | 5/2014 | Reis et al. |
| 8,746,252 B2 | 6/2014 | McGrogan et al. |
| 8,758,231 B2 | 6/2014 | Bunch et al. |
| 8,827,947 B2 | 9/2014 | Bosman et al. |
| 8,827,948 B2 | 9/2014 | Romo et al. |
| 8,894,610 B2 | 11/2014 | MacNamara et al. |

(56) References Cited

U.S. PATENT DOCUMENTS

| | | |
|---|---|---|
| 8,961,533 B2 | 2/2015 | Stahler et al. |
| 9,173,713 B2 | 11/2015 | Hart et al. |
| 9,186,046 B2 | 11/2015 | Ramamurthy et al. |
| 9,204,933 B2 | 12/2015 | Reis et al. |
| 9,226,796 B2 | 1/2016 | Bowling |
| 9,254,123 B2 | 2/2016 | Alvarez et al. |
| 9,314,953 B2 | 4/2016 | Lauer |
| 9,408,669 B2 | 8/2016 | Kokish et al. |
| 9,427,551 B2 | 8/2016 | Leeflang et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,439 B2 | 11/2019 | Joseph et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,555,780 B2 | 2/2020 | Tanner et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,720 B2 | 6/2020 | Wong et al. |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,792,464 B2 | 10/2020 | Romo et al. |
| 2001/0004676 A1 | 6/2001 | Ouchi |
| 2002/0045905 A1 | 4/2002 | Gerbi et al. |
| 2003/0036748 A1 | 2/2003 | Cooper et al. |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0030349 A1 | 2/2004 | Boukhny |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0193013 A1 | 9/2004 | Isakawa et al. |
| 2004/0249246 A1 | 12/2004 | Campos |
| 2004/0257021 A1 | 12/2004 | Chang et al. |
| 2005/0004515 A1 | 1/2005 | Hart et al. |
| 2005/0070844 A1 | 3/2005 | Chow et al. |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad |
| 2005/0222581 A1 | 10/2005 | Fischer et al. |
| 2005/0222714 A1 | 10/2005 | Nihei et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0253108 A1 | 11/2006 | Yu et al. |
| 2006/0264708 A1 | 11/2006 | Horne |
| 2006/0276827 A1 | 12/2006 | Mitelberg et al. |
| 2007/0032906 A1 | 2/2007 | Sutherland et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2007/0299427 A1 | 12/2007 | Yeung et al. |
| 2008/0006503 A1 | 1/2008 | Cooper |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0065109 A1 | 3/2008 | Larkin |
| 2008/0097293 A1 | 4/2008 | Chin et al. |
| 2008/0108869 A1 | 5/2008 | Sanders et al. |
| 2008/0114341 A1 | 5/2008 | Thyzel |
| 2008/0139887 A1 | 6/2008 | Fitpatrick |
| 2008/0146874 A1 | 6/2008 | Miller |
| 2008/0147089 A1 | 6/2008 | Loh |
| 2008/0177285 A1 | 7/2008 | Brock et al. |
| 2008/0187101 A1 | 8/2008 | Gertner |
| 2008/0208001 A1 | 8/2008 | Hadani |
| 2008/0212082 A1 | 9/2008 | Froggatt et al. |
| 2008/0214925 A1 | 9/2008 | Wilson et al. |
| 2008/0218770 A1 | 9/2008 | Moll et al. |
| 2008/0228104 A1 | 9/2008 | Uber et al. |
| 2008/0231221 A1 | 9/2008 | Ogawa |
| 2008/0287918 A1 | 11/2008 | Rosenman et al. |

(56) References Cited

U.S. PATENT DOCUMENTS

| | | |
|---|---|---|
| 2009/0099420 A1 | 4/2009 | Woodley et al. |
| 2009/0163851 A1 | 6/2009 | Holloway |
| 2009/0171271 A1 | 7/2009 | Webster et al. |
| 2009/0247880 A1 | 10/2009 | Naruse et al. |
| 2009/0248041 A1 | 10/2009 | Williams et al. |
| 2009/0248043 A1 | 10/2009 | Tierney et al. |
| 2009/0254083 A1 | 10/2009 | Wallace et al. |
| 2009/0262109 A1 | 10/2009 | Markowitz et al. |
| 2009/0264878 A1 | 10/2009 | Carmel et al. |
| 2009/0268015 A1 | 10/2009 | Scott et al. |
| 2009/0287354 A1 | 11/2009 | Choi |
| 2009/0299344 A1 | 12/2009 | Lee et al. |
| 2009/0306587 A1 | 12/2009 | Milijasevic et al. |
| 2009/0312768 A1 | 12/2009 | Hawkins et al. |
| 2009/0326322 A1 | 12/2009 | Diolaiti |
| 2010/0030023 A1 | 2/2010 | Yoshie |
| 2010/0036294 A1 | 2/2010 | Mantell et al. |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0228191 A1 | 9/2010 | Alvarez et al. |
| 2010/0249497 A1 | 9/2010 | Peine et al. |
| 2010/0249506 A1 | 9/2010 | Prisco et al. |
| 2010/0256812 A1 | 10/2010 | Tsusaka et al. |
| 2010/0331856 A1 | 12/2010 | Carlson et al. |
| 2011/0009779 A1 | 1/2011 | Romano et al. |
| 2011/0009863 A1 | 1/2011 | Stanislaw |
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0106102 A1 | 5/2011 | Balicki et al. |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071752 A1 | 3/2012 | Sewell |
| 2012/0071821 A1 | 3/2012 | Yu |
| 2012/0071894 A1 | 3/2012 | Tanner et al. |
| 2012/0071895 A1 | 3/2012 | Stabler et al. |
| 2012/0123327 A1* | 5/2012 | Miller ............... A61M 25/0136 604/95.04 |
| 2012/0136419 A1 | 5/2012 | Zarembo et al. |
| 2012/0138586 A1 | 6/2012 | Webster et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0325030 A1 | 12/2013 | Hourtash et al. |
| 2013/0345519 A1 | 12/2013 | Piskun et al. |
| 2014/0012276 A1 | 1/2014 | Alvarez |
| 2014/0012288 A1 | 1/2014 | Darisse |
| 2014/0046313 A1 | 2/2014 | Pederson et al. |
| 2014/0069437 A1 | 3/2014 | Reis et al. |
| 2014/0135985 A1 | 5/2014 | Coste-Maniere et al. |
| 2014/0142591 A1 | 5/2014 | Alvarez et al. |
| 2014/0200402 A1 | 7/2014 | Snoke et al. |
| 2014/0222019 A1 | 8/2014 | Brudnick |
| 2014/0222207 A1 | 8/2014 | Bowling et al. |
| 2014/0235943 A1 | 8/2014 | Paris |
| 2014/0276391 A1 | 9/2014 | Yu |
| 2014/0276594 A1 | 9/2014 | Tanner et al. |
| 2014/0296870 A1 | 10/2014 | Stern et al. |
| 2014/0309649 A1 | 10/2014 | Alvarez et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0025539 A1 | 1/2015 | Alvarez et al. |
| 2015/0031950 A1 | 1/2015 | Drontle et al. |
| 2015/0051592 A1 | 2/2015 | Kintz |
| 2015/0101442 A1 | 4/2015 | Romo |
| 2015/0104284 A1 | 4/2015 | Riedel |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0255782 A1 | 9/2015 | Kim et al. |
| 2015/0335480 A1 | 11/2015 | Alvarez et al. |
| 2015/0342695 A1 | 12/2015 | He |
| 2015/0359597 A1 | 12/2015 | Gombert et al. |
| 2016/0000414 A1 | 1/2016 | Brown |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0151122 A1 | 6/2016 | Alvarez et al. |
| 2016/0183841 A1 | 6/2016 | Duindam et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0372743 A1 | 12/2016 | Cho et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0281218 A1 | 10/2017 | Timm |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |

(56) References Cited

U.S. PATENT DOCUMENTS

| | | |
|---|---|---|
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 1857877 | 11/2006 |
| CN | 101500470 A | 8/2009 |
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| EP | 0904796 B1 | 11/2004 |
| EP | 2 392 435 | 12/2011 |
| JP | 09-224951 | 9/1997 |
| JP | 2006-525087 | 11/2006 |
| JP | 2007-511247 | 5/2007 |
| JP | 2009-139187 | 6/2009 |
| JP | 2010-046384 | 3/2010 |
| JP | 2011-015992 | 1/2011 |
| JP | 2012-105793 | 6/2012 |
| WO | WO 92/14411 | 9/1992 |
| WO | WO 94/14494 | 7/1994 |
| WO | WO 00/67640 | 11/2000 |
| WO | 0159643 A1 | 8/2001 |
| WO | WO 02/74178 | 9/2002 |
| WO | WO 03/096871 | 11/2003 |
| WO | WO 04/039273 | 5/2004 |
| WO | 2004096015 A2 | 11/2004 |
| WO | 2004103430 A2 | 12/2004 |
| WO | WO 04/105849 | 12/2004 |
| WO | WO 05/032637 | 4/2005 |
| WO | 2004114037 A3 | 9/2005 |
| WO | WO 05/081202 | 9/2005 |
| WO | WO 09/097461 | 6/2007 |
| WO | 2007146987 A2 | 12/2007 |
| WO | WO 07/146987 | 12/2007 |
| WO | WO 08/097540 | 8/2008 |
| WO | WO 09/092059 | 7/2009 |
| WO | WO 10/068005 | 6/2010 |
| WO | WO 10/081187 | 7/2010 |
| WO | 2010088187 A1 | 8/2010 |
| WO | 2010093153 A2 | 8/2010 |
| WO | 2010133733 A1 | 11/2010 |
| WO | WO 11/005335 | 1/2011 |
| WO | 2011058530 A1 | 5/2011 |
| WO | 2011100110 A1 | 8/2011 |
| WO | WO 11/161218 | 12/2011 |
| WO | 2013071071 A1 | 5/2013 |
| WO | WO 13/107468 | 7/2013 |
| WO | WO 15/093602 | 12/2013 |
| WO | WO 15/153111 | 10/2015 |
| WO | WO 16/003052 | 1/2016 |

OTHER PUBLICATIONS

Ehlers, et al. Integration of a spectral domain optical coherence tomography system into a surgical microscope for intraoperative imaging. Investigative Ophthalmology and Visual Science 52.6. 2011; 3153-3159.

Hubschman. Robotic Eye Surgery: Past, Present, and Future. Journal of Computer Science and Systems Biology. 2012.

Stoyanov, Oct. 20, 2011, Surgical Vision, Annals of Biomedical Engineering 40(2):332-345.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

European search report and search opinion dated Jul. 2, 2015 for EP Application No. 12856685.8.

Extended European Search Report dated Feb. 8, 2017 in patent application No. 14856482.6.

International search report and written opinion dated Nov. 7, 2014 for PCT Application No. PCT/US2014/041990.

International search report and written opinion dated Mar. 29, 2013 for PCT/US2012/069540.

International search report and written opinion dated Jan. 27, 2015 for PCT Application No. PCT/US2014/062284.

International Search Report and Written Opinion, PCT Application No. PCT/US15/53306, dated Feb. 4, 2016, 19 pages.

International Search Report and Written Opinion dated Jan. 10, 2017 in PCT/US16/051154.

Final Rejection for U.S. Appl. No. 14/583,021, dated Aug. 7, 2019, 11 pages.

(56) References Cited

OTHER PUBLICATIONS

Final Rejection for U.S. Appl. No. 14/583,021, dated May 18, 2018, 9 pages.
International Search Report dated Jun. 16, 2014 for PCT/US2014/022424, 3 pages.
Non-Final Rejection for U.S. Appl. No. 14/583,021, dated Aug. 28, 2017, 9 pages.
Non-Final Rejection for U.S. Appl. No. 14/583,021, dated Dec. 13, 2018, 8 pages.
Notice of Allowance for U.S. Appl. No. 14/583,021, dated May 15, 2020, 8 pages.
Notice of Allowance for U.S. Appl. No. 14/583,021, dated Sep. 11, 2020, 6 pages.
Office action dated Jun. 11, 2015 for U.S. Appl. No. 14/158,548, 10 pages.
Office action dated May 21, 2015 for U.S. Appl. No. 13/711,440, 14 pages.

* cited by examiner

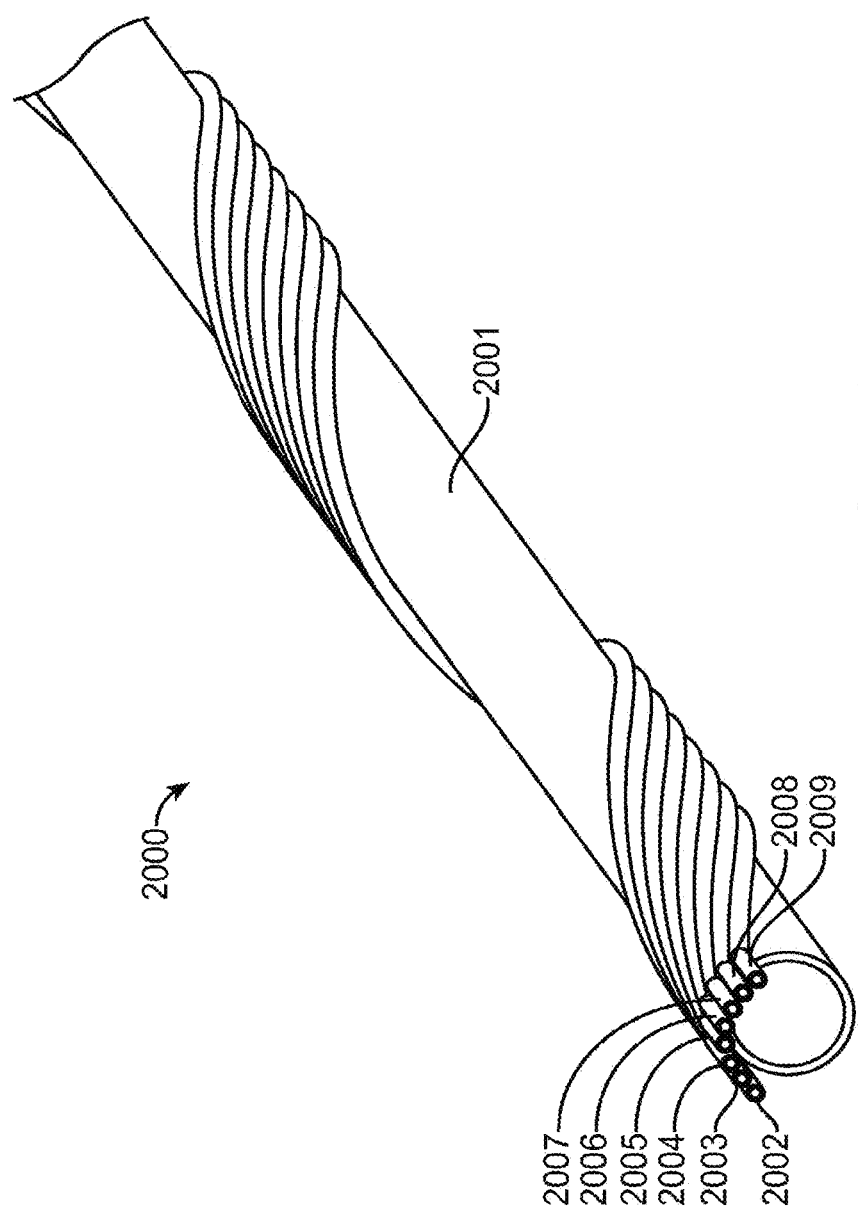

TOOL AND METHOD FOR USING SURGICAL ENDOSCOPE WITH SPIRAL LUMENS

CROSS-REFERENCE TO RELATED APPLICATIONS

This application is a divisional of U.S. patent application Ser. No. 14/583,021, filed Dec. 24, 2014, which claims the benefit of U.S. Provisional Application No. 62/019,816, filed Jul. 1, 2014, and U.S. Provisional No. 62/057,936, filed Sep. 30, 2014, the entire contents of each of which are incorporated herein by reference.

FIELD OF THE INVENTION

The field of the present application pertains to medical devices. More particularly, the field of the invention pertains to an endoscopic tool and related manufacturing techniques for use in robotically-assisted surgery.

BACKGROUND

Endoscopy is a widely-used, minimally invasive technique for both imaging and delivering therapeutics to anatomical locations within the human body. Typically a flexible endoscope is used to deliver tools to a remote operative site inside the body—e.g., through small incisions or a natural orifice in the body (nasal, anal, vaginal, urinary, throat, etc.)—where a procedure is performed. Endoscopes have imaging, lighting and steering capabilities at the distal end of a flexible shaft to enable navigation of non-linear lumens or pathways.

Early endoscopes utilized tendons along the length of the scope that terminate on a ring at the distal end. Tensioning those tendons on the proximal end results in actuating the endoscope at the distal end, causing it to bend in desired directions. The user determined the desired direction from images obtained from the distal end (e.g., CCD camera).

Early endoscopes were handheld devices with numerous levers and buttons for performing various functionalities. They were, however, challenging to steer and navigate. Surgeons had to contort their hands and arms when using the device to navigate the scope to the desired position. Additionally, early scopes required support personnel to both deliver, operate and remove operative, diagnostic or therapeutic devices from the scope while a surgeon maintained the desired position. In addition to these ergonomic issues, these scopes required fluoroscopy or segmented CT scans to assist in navigating to the desired location, particularly for small lumen navigation.

In addition, catheter-based surgical solutions utilize pull wires that have exhibit undesirable properties such as curve alignment and muscling. For example, in muscling, applying force to a given pull wire typically results in non-localized compressive force, resulting in articulation along the entire shaft, rather than just the distal tip.

Therefore, it would be beneficial to have improved control over catheters and endoscopes such that the neutral axis remains constant during bending operations. Additionally, it would be beneficial to have an improved method for manufacturing such catheters and endoscopes, i.e., endoscopes and catheters that maintain a neutral axis despite the bending, stretching, and articulating that occurs during use in anatomical structures and spaces.

SUMMARY OF THE INVENTION

Embodiments described herein are related to a method, apparatus, system, and tools for robotic surgery. Embodiments also include manufacturing methods for tools that may be used in robotic surgery.

In one aspect, the present invention provides for an elongated medical device comprising a hypotube backbone running through the device, and a spiral lumen spiraled around the backbone along the length of the backbone. In related devices, the backbone may be formed from a nitinol alloy. In related devices, the backbone may be configured to provide axial stiffness along the length of the device. In related devices, the device may comprise a jacket around the hypotube and spiral lumen. In related devices, the jacket may be formed using either melting, molding, bonding, or casting.

In related devices, the backbone may provide for a central lumen that runs the length of the device. In related devices, the backbone may be configured to deliver a central payload from the proximal end of the device to the distal end. In related devices, the central payload may be either laser fibers, microsurgical tools, imaging means, irrigation means, or aspiration means.

In related devices, the spiral lumen may be configured to deliver a spiral payload from the proximal end of the device to the distal end. In related devices, the spiral payload may be either laser fibers, microsurgical tools, imaging means, irrigation means, or aspiration means. In related devices, the inside diameter of the spiral lumen may be smaller than the inside diameter of the central lumen.

In another aspect, the present invention provides for an endoscopic method that comprises providing an elongated medical device that comprises a hypotube backbone running along the length of the device and a spiral lumen spiraled around the backbone along the length of the device, directing the device into an anatomical lumen, and positioning the device at a desired operative region through the anatomical lumen. In related methods, the backbone may be formed from a nitinol alloy. In related methods, the backbone may be configured to provide axial stiffness along the length of the device. In related methods, a jacket may surround the hypotube and spiral lumen.

In a related method, the backbone may provide a central lumen that runs along the length of the device. In a related method, the central lumen may be configured to deliver a central payload from the proximal end of the device to the distal end. In a related method, the central payload may be either laser fibers, microsurgical tools, imaging means, irrigation means, or aspiration means. In a related method, the spiral lumen may be configured to deliver a spiral payload from the proximal end of the device to the distal end. In a related method, the spiral payload may be either laser fibers, microsurgical tools, imaging means, irrigation means, or aspiration means.

An embodiment of the present invention provides a sheath with a lumen therethrough, having a controllable and articulable distal end, which is mounted to a first robotic arm having at least 3 DOF, but preferably 6 or more DOF. This embodiment also includes a flexible endoscope having a controllable and articulable distal end, a light source and video capture unit at the distal end thereof, and at least one working channel extending therethrough. The flexible endoscope is slidingly disposed in the lumen of the sheath, and is mounted to a second robotic arm having at least 3 DOF, but preferably 6 or more DOF. Further included are first and second modules, operatively coupled, respectfully, to the proximal ends of the sheath and flexible endoscope. The modules are mounted to the first and second robotic arms, thereby mounting the sheath and flexible endoscope to first and second robotic arms, respectively. The modules provide the mechanics to steer and operate the sheath and flexible endoscope, and receive power and other utilities from the robotic arms. The robotic arms are positioned such that the first module is distal to the second module and the proximal end of the sheath is distal to the proximal end of the flexible endoscope. Movement of the first and second robotic arms relative to each other and relative to the patient causes movement of the sheath relative to the flexible endoscope and movement of either relative to the patient.

In one embodiment the robots are positioned relative to each other such that the sheath and flexible endoscope are in a substantially straight (e.g., approximately 180 degree angle), co-axially aligned configuration between the first and second robotic arms, forming a "virtual rail" between the robotic arms. It is to be noted that the virtual rail may take on angles ranging from 90-180 degrees. Movement of the robotic arms relative to each other provide axial motion of the sheath and flexible endoscope relative to each other and the patient, while maintaining the virtual rail between the robotic arms.

The first and second robotic arms may be on separate mobile carts or on the same mobile cart. The mobile carts permit transporting the arms between procedure rooms or moving within a procedure room to better accommodate necessary equipment and the patient bead. Alternatively, though less preferred, the robotic arms could be fixed to the floor or bed.

The present invention alternatively provides multiple modules for different procedures, where the robotic arms retrieve a desired module from a storage place, e.g., a module exchange table or stand, located in the procedure room. Each module or module pair is designed for a specific type of procedure.

The modules with the sheath and flexible endoscope combination can navigate narrow lumens within the human body (e.g., bronchial and other lung airways, blood vessels, urinary tract inter alia). Additional modules may include laparoscopic (single or dual port), microsurgical modules (which may also have a sheath and flexible endoscope arrangement, but sized appropriately for the eye or other microsurgical site). Alternatively the microsurgical modules may be configured to hold rigid instruments sized appropriately for the scale of the surgery.

In embodiments in accordance with the present invention the sheath and flexible endoscope comprising a shaft having a proximal end, a distal end and a controllable bending section, where preferably the controllable bending section is a distal bending section. At least one tendon-conduit, preferably four extend through a wall of the shaft wall from the proximal end to a distal portion of the controllable bending section, preferably the distal end. Preferably, the shaft has an approximate circular or elliptical cross section. At least one tendon, preferably four extend through each of the at least one tendon-conduits. The tendon-conduits extend through the shaft wall approximately parallel to a central axis of the shaft from the proximal end up to a helix section of the shaft, and where the tendon-conduits extend through the shaft wall in a helixed or spiral pattern relative to the central axis up to a proximal portion of the controllable bending sections, and where the tendon-conduits extend through the shaft wall approximately parallel to the central axis up to a distal portion of the controllable bending section. Preferably, the controllable bending section is at the distal end of the shaft. The at least on tendon is secured to the distal portion of the controllable bending section, such that tensioning the at least one tendon causes the controllable bending section to articulate.

BRIEF DESCRIPTION OF THE DRAWINGS

The invention will be described, by way of example, and with reference to the accompanying diagrammatic drawings, in which:

FIG. 20A illustrates an isometric view of a flexible endoscopic device with a hypotube backbone and non-uniformly spaced helixed lumens, in accordance with an embodiment of the present invention;

DETAILED DESCRIPTION OF THE INVENTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

Figure 1:
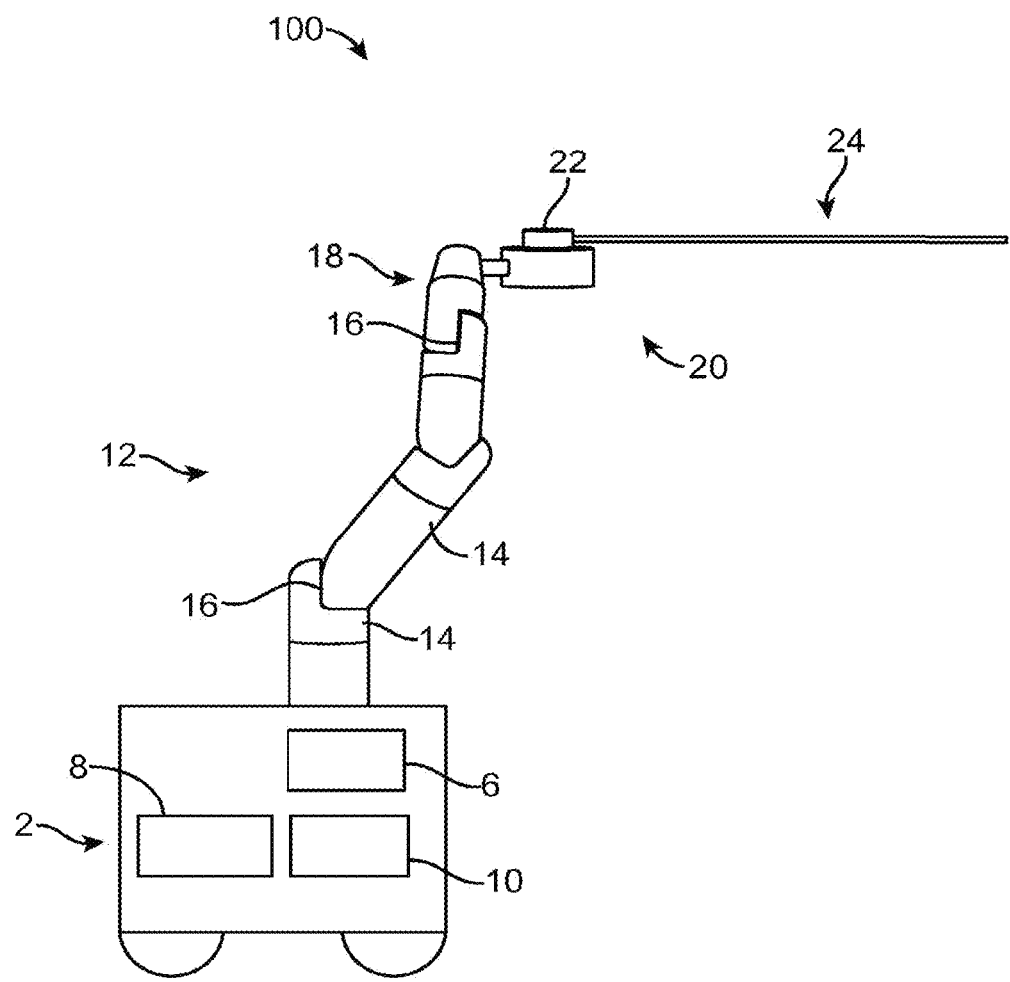
FIG. 1 illustrate a robotic surgical system in accordance with an embodiment of the present invention.

Referring to FIG. 1, a robotic surgical system 100 in accordance with an embodiment of the present invention is depicted. Cart 2 has wheels 4 provided for mobility, and has various utilities (e.g., pneumatic pressure 6, power 8, and central processing unit 10) for use by surgical system 100 during a procedure. Robotic arm 12 is mounted on cart 2, and has at least 3 degrees of freedom ("DOF"), and preferably 6 or more DOF. Robotic arm 12 is shown with only two arms/links 14 connected at joints 16, but it is preferred to have multiple arms/links 14, where each is connected at one or more joints to provide desired degrees of freedom at each joint. Module changer 18 is provided at the distal portion of the robotic arm, which is used to exchange instrument modules based on a desired procedure, as more thoroughly described below. Module 20, in one embodiment, connects to module changer and comprises instrument coupling 22 and instrument 24. Presently, it is preferred to use Kuka AG's LBR5 robotic arm with joint level torque sensing having a wrist at the distal end. This robot has 7 DOF. The preferred robotic arm for the present invention has 7 joints, with the redundant joint provided to avoid potential arm collision with a patient, other robot arms, operating table, medical personal or equipment proximate to the operative field, while maintaining the wrist at the same pose so as not to interrupt an ongoing procedure. The skilled artisan will appreciate that a robotic arm with at least 3 DOF, and more preferably 6 or more DOF will fall within the inventive concepts described herein, and further appreciate that more than one arm may be provided with additional modules, where each arm may be commonly or separately mounted on one or more carts.

Robotic surgical system 100 may be configured in a manner to provide a plurality of surgical system configurations, for example by changing modules 20 (in robotics parlance module 20 is also known as an end effector). The system may comprise one or more mobile robotic platforms, which are staged at different locations in the operative room, or at a convenient nearby location. Each platform may provide some or all of power, pneumatic pressure, illumination sources, data communication cables and control electronics for a robotic arm that is coupled to the platform, and the module may draw from these utilities as well. System 100 may alternatively have multiple robotic arms 12 mounted on one or more mobile carts 2, or the arms may be mounted to the floor in order to provide a plurality of surgical configurations.

Cart(s) 20 may be located in various locations in the operating room in order to accommodate space needs and facilitate appropriate placement and motion of modules and instruments with respect to a patient. This capability enables the arms to be positioned in locations where they do not interfere with the patient, doctor, anesthesiologist or any supportive surgical equipment required for the selected procedure. During procedures, the robotic arms with instruments will work collaboratively via user control through separate control devices, which may include (not by way of limitation) a master console with haptic devices, joystick, or customized pedants.

Figure 2A:
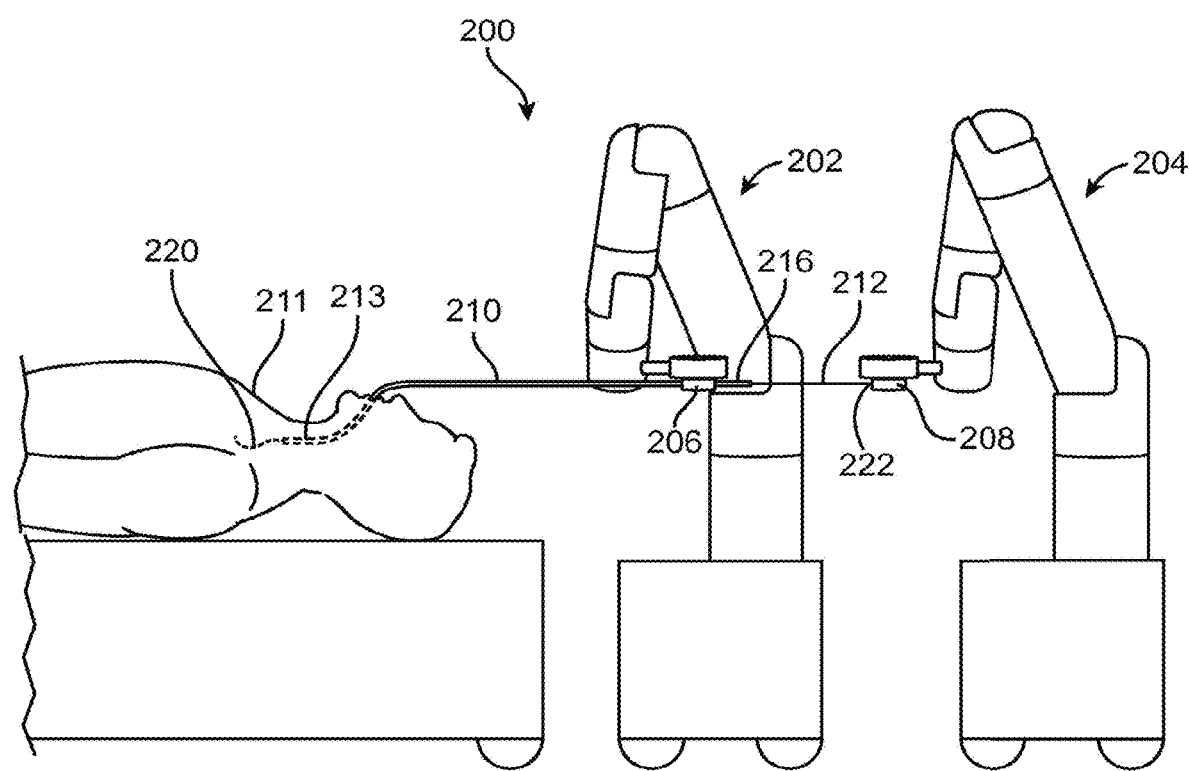
FIGS. 2A, 2B, 2C illustrate a dual arm robotic surgical system in accordance with an embodiment of the present invention.
Figure 2B:
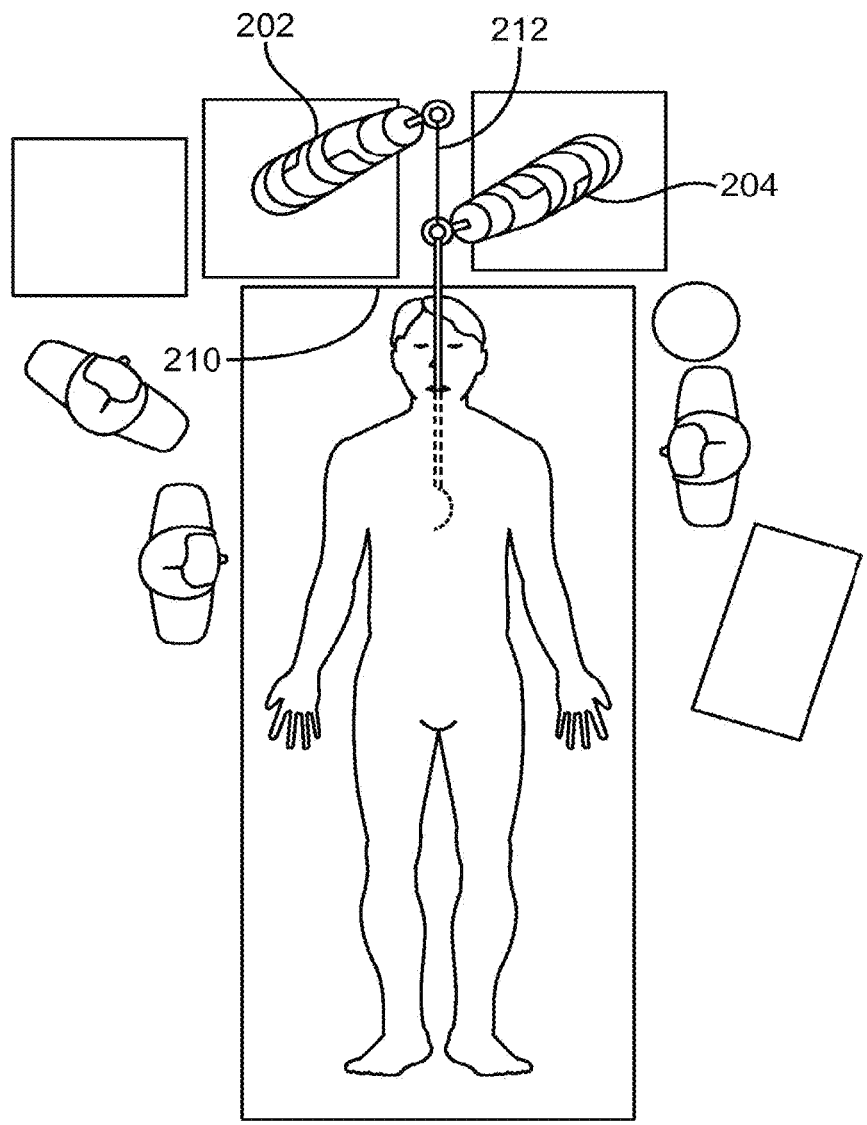

FIG. 2A shows robotic surgery system 200 in accordance with an embodiment of the present invention. System 200 has first and second robotic arms 202 and 204 holding modules 206 and 208, respectively. Module 206 has controllable sheath 210 operatively connected thereto. Module 208 has flexible endoscope 212 operatively connected thereto. FIG. 2B shows an overhead view of system 200 where anesthesia cart 201 is provided towards the head of the patient. Additionally, control console 203 with a user interface is provided to control sheath 210, flexible endoscope 212, and the associate robotic arms 202 and 204 and modules 206 and 208.

Robotic arms 202 and 204 align modules 206 and 208 such that proximal end 216 of sheath 210 is distal of the proximal end 222 of flexible endoscope 212, and such that endoscope 212 remains axially aligned with sheath 210 at an approximate angle of 180 degrees between the two robotic arms, resulting in a "virtual rail" where the rail is approximately straight, or at 180 degrees. As will be described later, the virtual rail may have angles between 90-180 degrees. In one embodiment, sheath 210, with flexible endoscope 212 slidingly disposed therethrough, is robotically inserted through, for example, a tracheal tube (not shown) in the mouth of and into patient 211, and ultimately into the patient's bronchial system, while continually maintaining the virtual rail during insertion and navigation. Robotic arms move sheath 210 and endoscope 212 axially relative to each other and in to or out of patient 211 under the control of a doctor (not shown) at a control console 203.

Navigation is achieved, for example, by advancing sheath 210 along with endoscope 212 into the patient, then endoscope 212 may be advanced beyond distal end 213 of the sheath, and the sheath may then be brought even with the endoscope, until a desired destination is reached. Other modes of navigation may be used, such as and not by way of limitation using a guide wire through the working channel of the endoscope. The physician may be using any number of visual guidance modalities or combination thereof to aid navigation and performing the medical procedure, e.g., fluoroscopy, video, CT, MR etc. Distal end 220 of flexible endoscope 212 is then navigated to an operative site and tools are deployed through tool channel 219 to perform desired procedures. The virtual rail is maintained during the navigation procedure and any subsequent operative procedures. Any number of alternative procedures that may require a tool or no tool at all can be performed using the flexible endoscope sliding through the sheath, as the skilled artisan will appreciate.

Figure 2C:
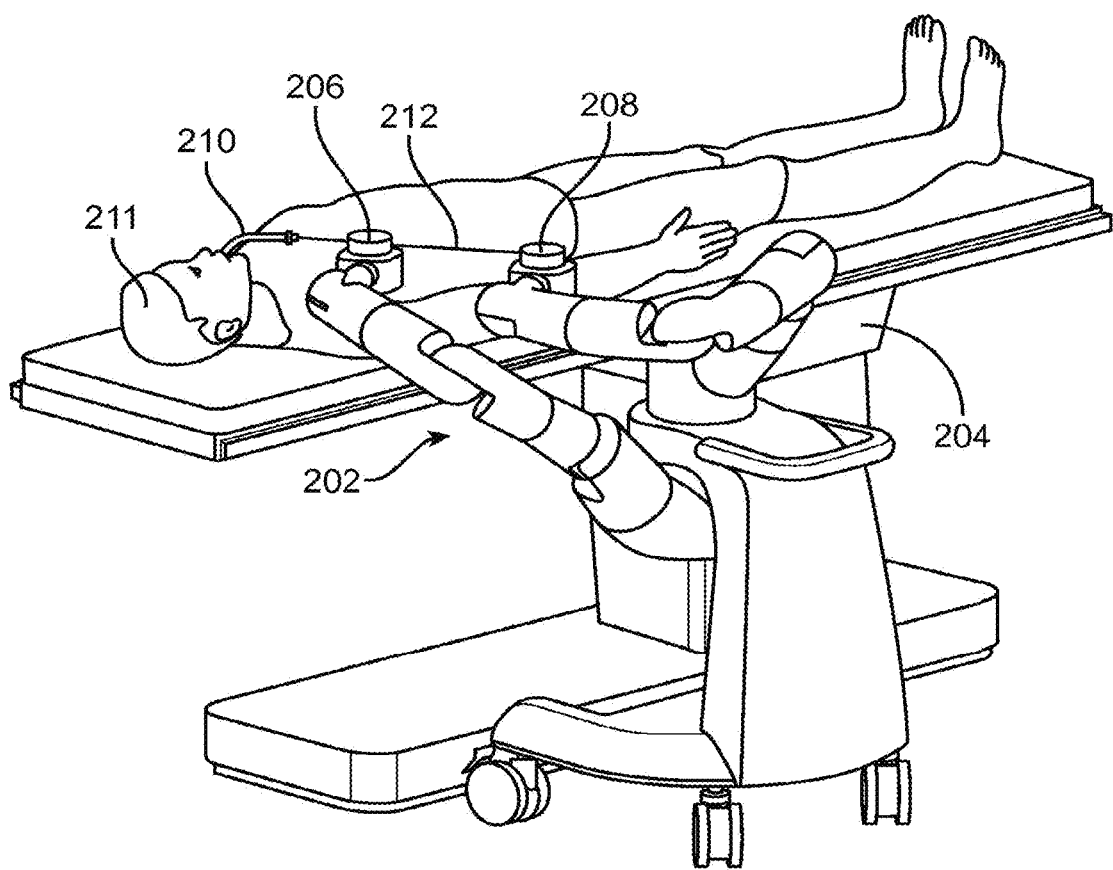

FIG. 2C shows an isometric view of system 200 in FIG. 2A. Modules 206 and 208 with associated sheath 210 and endoscope 212 are attached to robotic arms 202 and 204 and arranged in a 180 degree virtual rail. The robotic arms are shown on a single cart, which provides added compactness and mobility. It will be appreciated that modules 206 and 208 have pulley systems or other actuation systems to tension tendons 228 (not shown) in sheath 210 and endoscope 212 to steer their respective distal ends. Modules 206 and 208, particularly 208, provide other desired utilities for the sheath and endoscope, such as pneumatic pressure, electrical, data communication (e.g., for vision), mechanical actuation (e.g., motor driven axels) and the like. These utilities may be provided to the modules through the robotic arms, from a separate source or a combination of both.

Figure 2D:
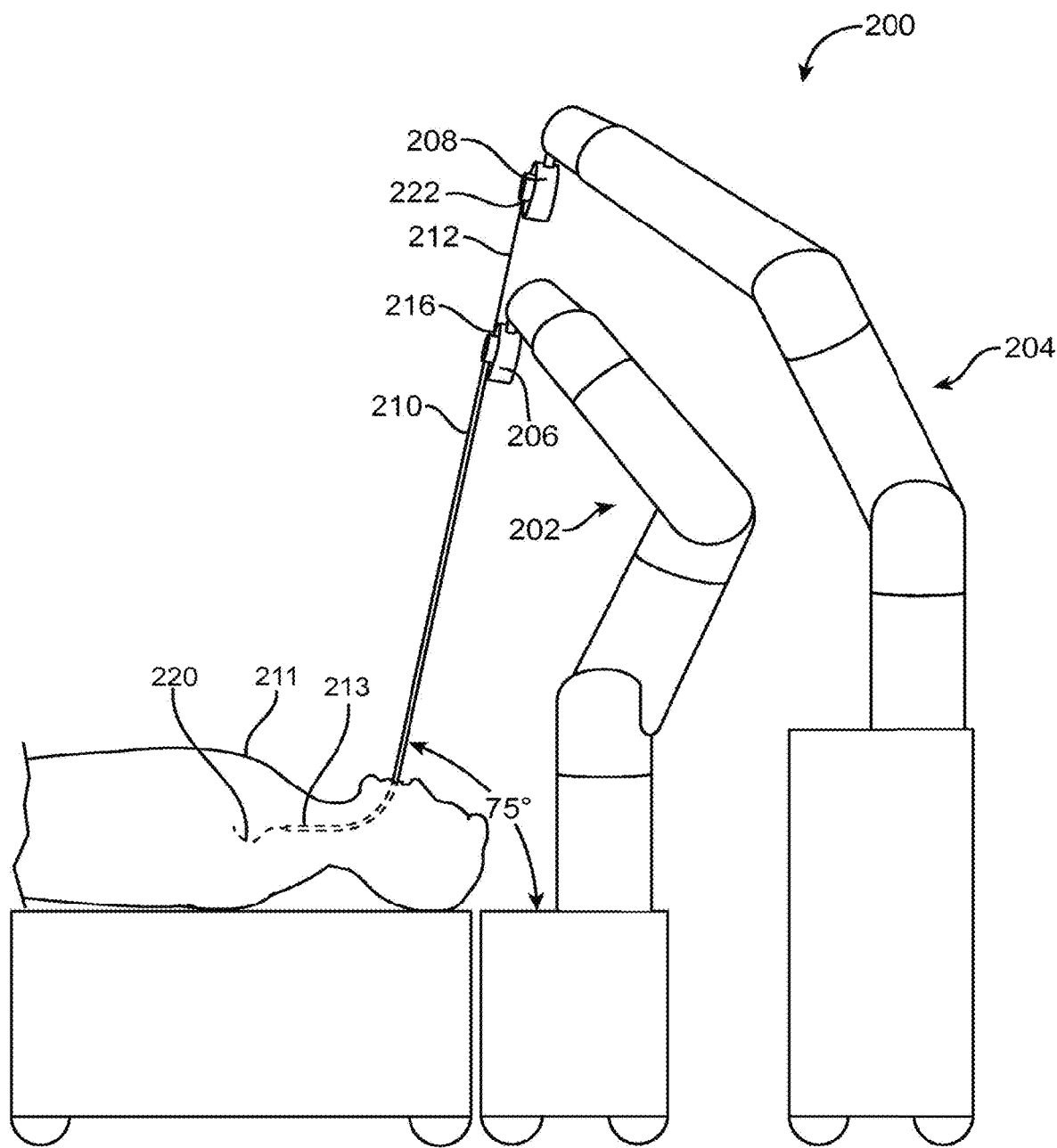
FIGS. 2D, 2E illustrate alternate embodiments of a robotic surgical system of the present invention.
Figure 2E:
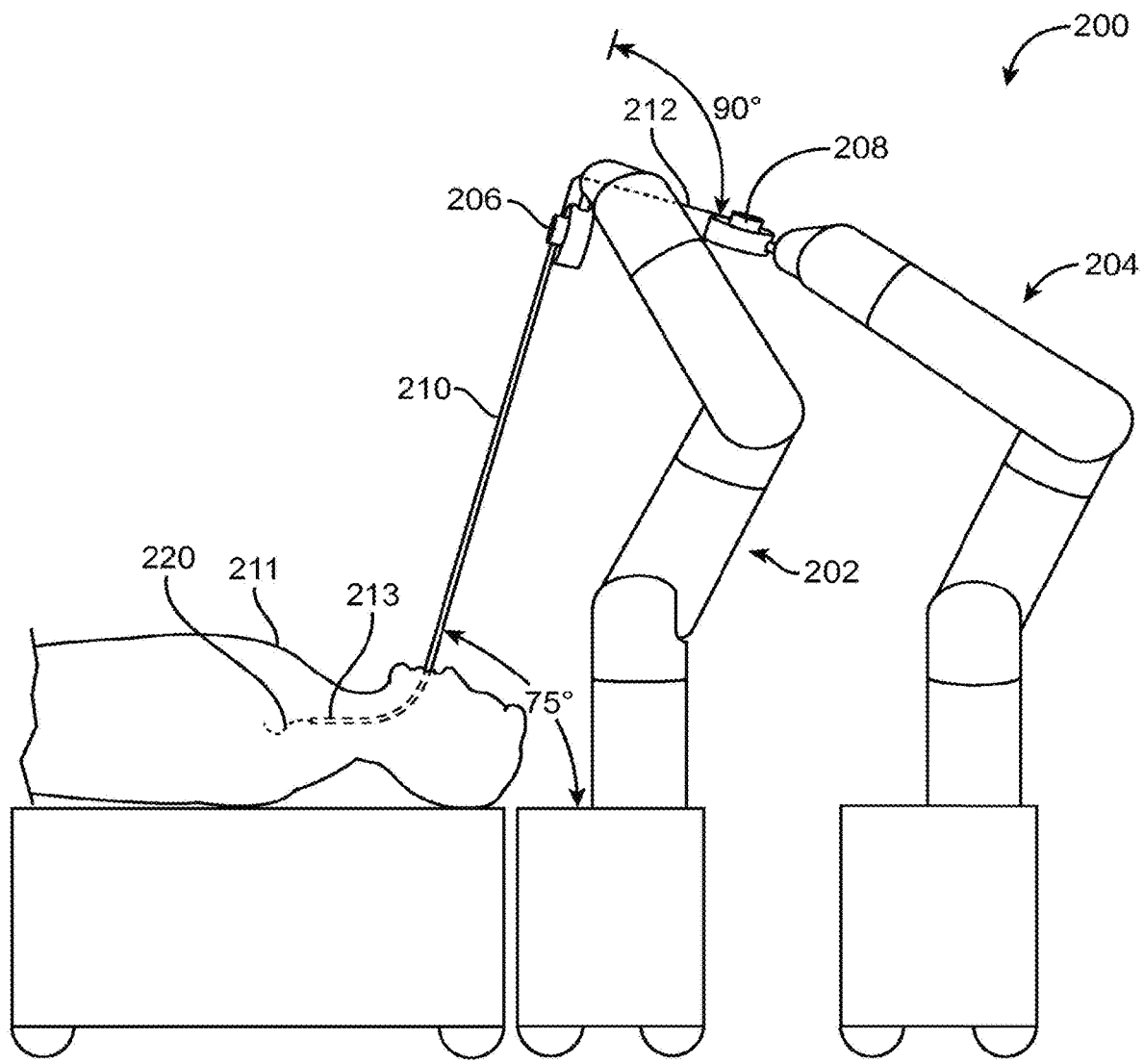

FIGS. 2D and 2E provide alternative arrangements of robotic arms 202 and 204 showing the versatility of the robotic surgical system in accordance with embodiments of the present invention. In FIG. 2D, robotic arms 202 and 204 are extended to have the instrument enter the patient's mouth at 75 degrees from horizontal, while still maintaining a 180 degree virtual rail. This may be done during the procedure if circumstances require such, and/or may be done to accommodate space requirements within the room. The 75 degree angle was chosen for demonstrative purposes, not by way of limitation. FIG. 2E shows an alternative arrangement where the virtual rail is at 90 degrees and the instrument enters the patient's mouth at 75 degrees from horizontal.

In some embodiments, the robotic arms can manipulate the mechanism in a controlled fashion to create virtual rails. Such rails are useful in driving both rigid instrument and flexible instruments, and especially instruments which are telescoping or have other interaction requirements. The virtual rail is not limited to a single rail but can consist of multiple virtual rails where the robotic arms act in concert to maintain the individual virtual rails in performance of one or more procedures.

Figure 3A:
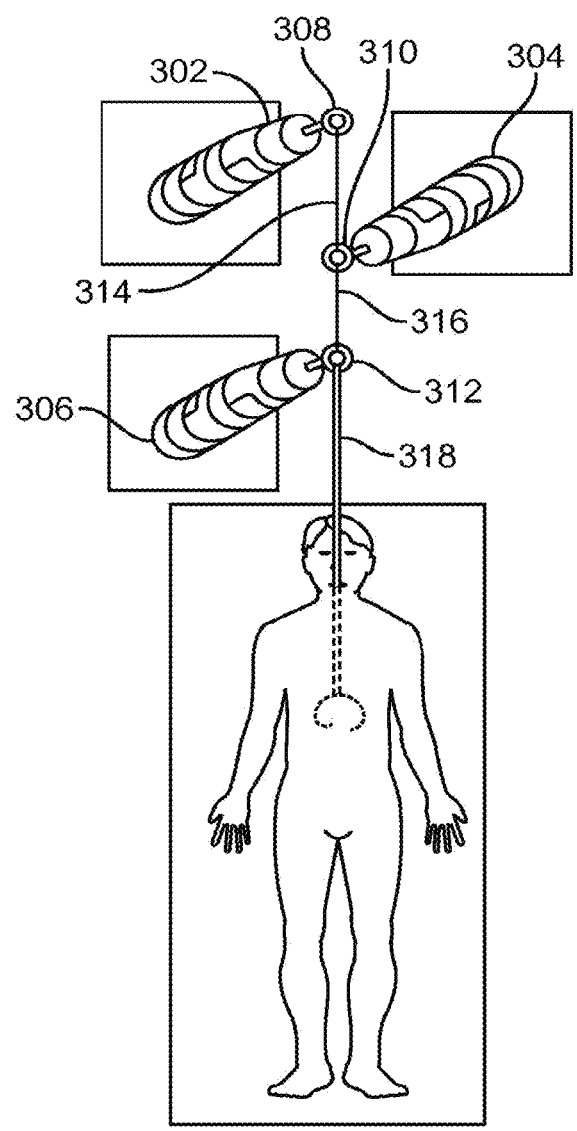
FIGS. 3A, 3B illustrate alternate configurations of multiple robotic arms and multiple virtual rails, in accordance with embodiments of the present invention.

FIG. 3A shows an overhead view of a system with multiple virtual rails, in an accordance with an embodiment of the present invention. In FIG. 3A, robot arms 302, 304 and 306 respectively hold modules 308, 310, and 312. Modules 308 and 310 are each operatively coupled to flexible instrument 314 and instrument 316. For example instrument 314 may be a flexible endoscope and instrument 316 may be a telerobotically controlled instrument, which is a matter of choice for the purpose of explanation and not by way of limitation. Module 318 is operatively coupled to a dual lumen sheath 318, where each lumen receives instruments 314 and 316. Robotic arms 302 and 304 each maintain a virtual rail with robotic arm 316, and movements of all three robotic arms are coordinated to maintain the virtual rails and to move instruments 314, 316 and sheath 312 relative to each other and the patient.

Figure 3B:
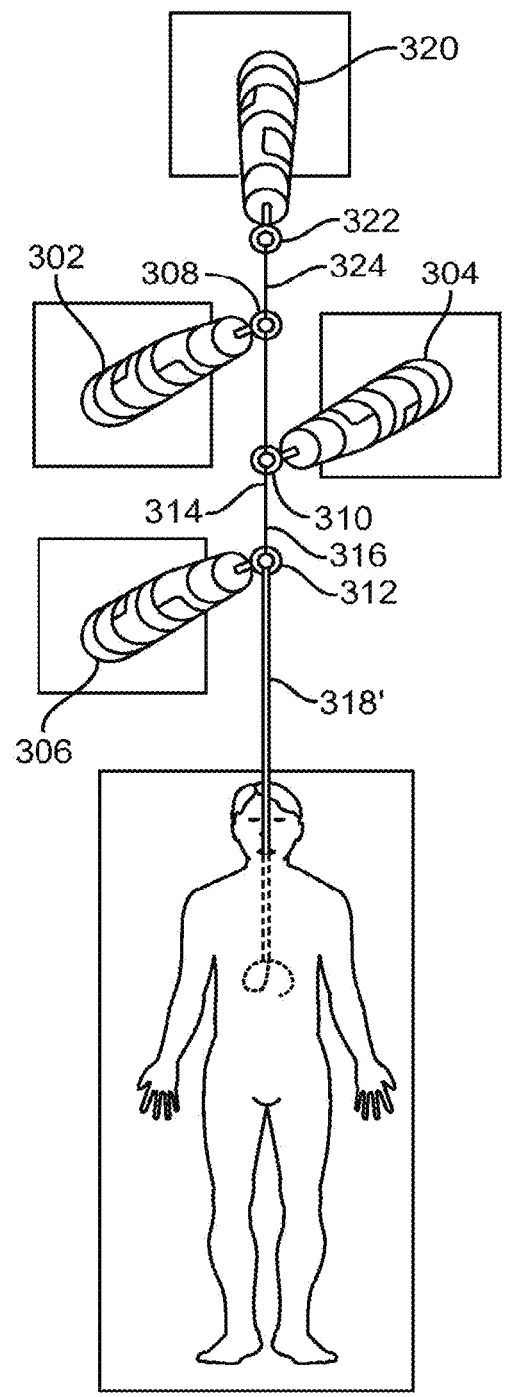

FIG. 3B is an embodiment with a fourth robotic arm 320 with associated module 322 and instrument 324. In this embodiment sheath 318' would have three lumens or alternatively sheath 318' may be more than one sheath to provide access to instruments 314, 316, and 324. As will be appreciated, the ability to increase or reduce the number of robotic arms with associated modules and instruments permits a great number and flexibility of surgical configurations, which, in turn, permits repurposing of expensive robotic arms and use a multiple relatively inexpensive modules thereby achieving great versatility at reduced expense for the advantage of robotically controlled surgical procedures.

To create the virtual rail, a plurality of arms and/or platforms may be utilized. Each platform/arm must be registered to the others, which can be achieved by a plurality of modalities including, vision, laser, mechanical, magnetic, or rigid attachment. In one embodiment, registration may be achieved by a multi-armed device with a single base using mechanical registration. In mechanical registration, an embodiment may register arm/platform placement, position, and orientation based on their position, orientation and placement relative to the single base. In another embodiment, registration may be achieved by a system with multiple base using individual base registration and "handshaking" between multiple robot arms. In embodiments with multiple bases, registration can be achieved by touching together arms from different bases, and calculating locations, orientation and placement based on that contact and the relative locations of those bases. In some embodiments, registration targets may be used to match the position and orientations of the arms relative to each other. Through such registration, the arms and instrument driving mechanisms may be calculated in space relative to each other. The skilled artisan will be able to use many different methods to register the robotic platforms.

System Modularity & Flexibility

In addition to multiple arms and platforms, certain embodiments of the present invention are designed to readily exchange between multiple modules or end effector mechanisms. Various surgical procedures or steps within a procedure may require the use of different modules and the associated instrument sets, for example, exchanging between different sized sheath and endoscope combinations. The interchangeability allows the system to reconfigure for different clinical procedures or adjustments to surgical approaches.

Figure 4A:
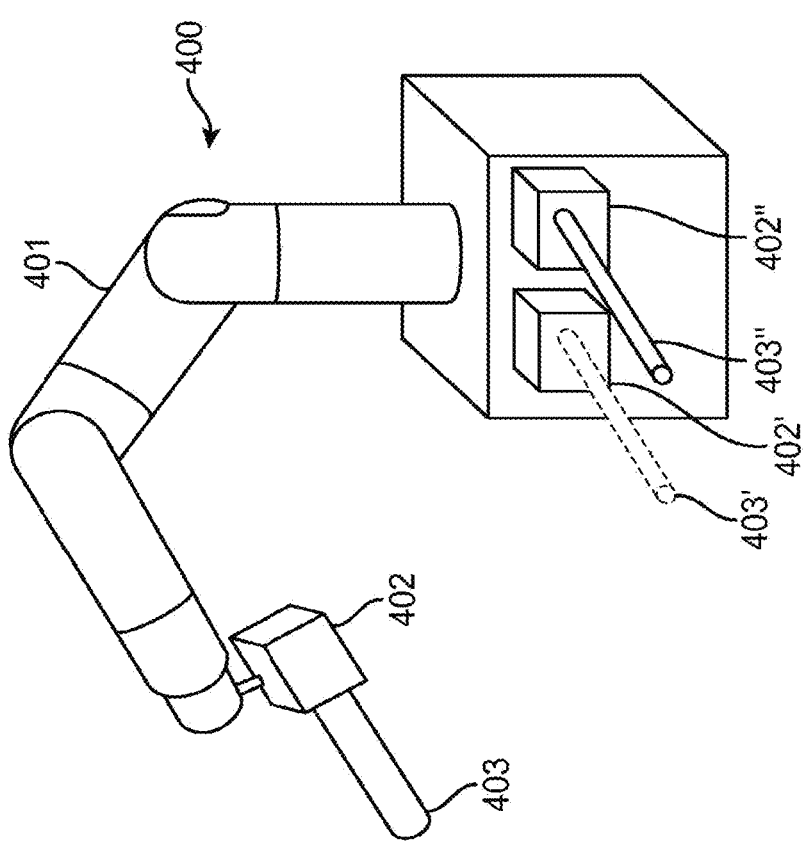
FIGS. 4A, 4B illustrate modularity of an embodiments of the present invention.

FIG. 4A illustrates an embodiment compatible with interchangeable modules and instruments. Surgical system 400, like those shown and described previously, has one or more robotic arms 401 to which module 402 with instrument 403 is attached. Modules 402' and 402", and associated instruments 403' and 403", can be exchanged onto robotic arm 401 or picked up by a different robotic arm (not shown) to be used alone in concert with another module. Each module is a dedicated electromechanical system which is used to drive various types of instruments for specified procedures. They may contain sensors (e.g., RFID) or memory chips that record their calibration and application related information. A system calibration check may be required after a new mechanism is connected to the robot arm. In some embodiments, a module may control an associated sheath or flexible endoscope.

Figure 4B:
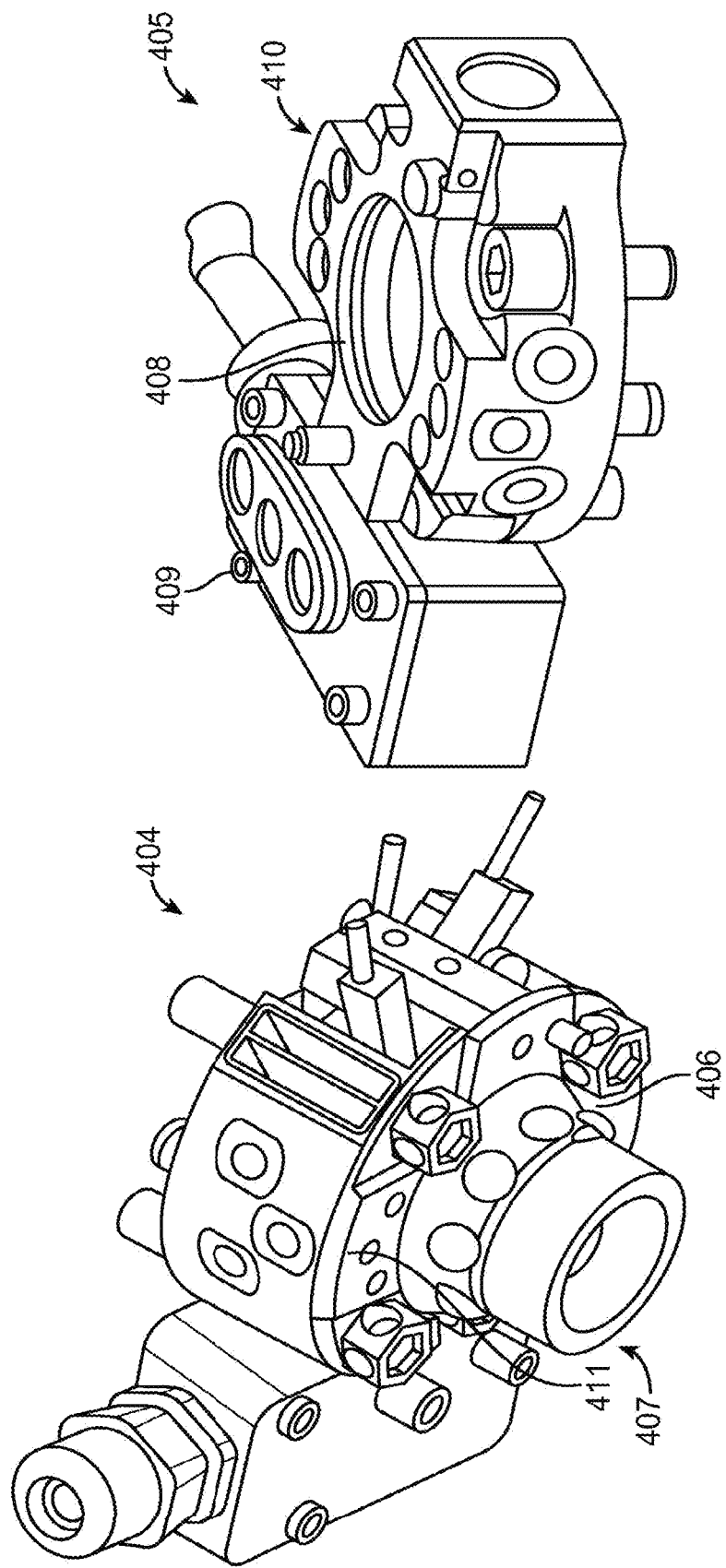

FIG. 4B shows two different perspectives on exchange mechanisms 404 and 405 that may be used to exchange and attach modules 402 to robotic arm 401. Exchange mechanisms 404 and 405 provide the connection between a module, such as module 402 in FIG. 4A, and a robotic arm, such as robotic arm 401 in FIG. 4A. In some embodiments, the mechanism 404 may be the interface on a module, such as an instrument driving mechanism, for connection to mechanism 405, which may be the interface on a robotic arm. Mechanism 404 may provide a mechanism interface 411 for connecting flange 407 into ring 408 of mechanism 405. Similarly, the interface may provide for transmitting power (409), fiber optics, data connections, pneumatic connections (410, 411), motors to drive pulley systems to control a tool, such as a sheath and flexible endoscope. As described for the sheath and flexible endoscope embodiment, the sheath and flexible endoscope would be operatively coupled to the exchange mechanism.

Figure 5:
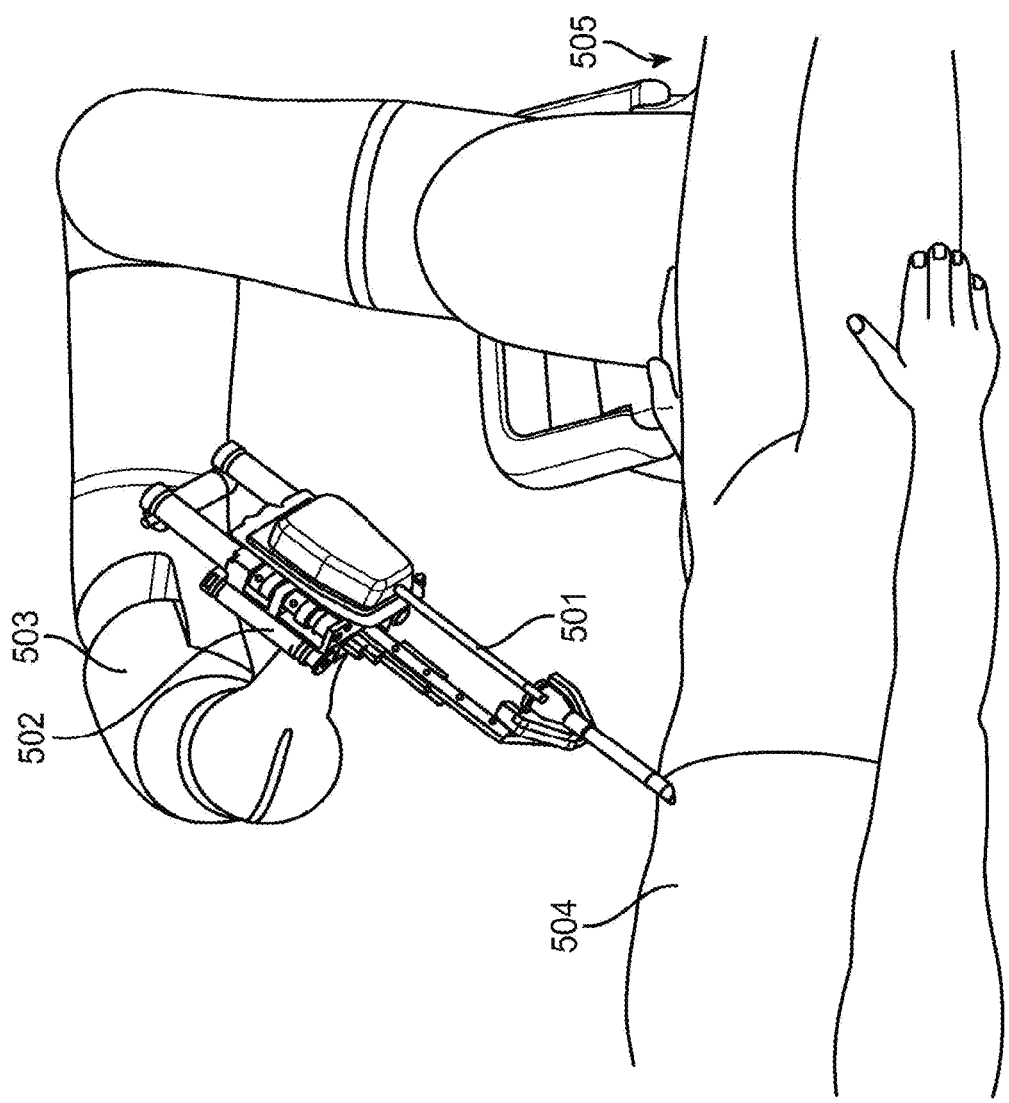
FIGS. 5 and 6 illustrate alternative embodiments of modules for the robotic surgical system of the present invention.

FIGS. 5-8 illustrate additional, interchangeable modules that may be operated using system 400 from FIG. 4. FIG. 5 illustrates an embodiment of the present invention that uses a single port laparoscopic instrument 501 connected through an instrument interface 502 on a single robotic arm 503 that is directed at the abdomen 504 of a patient 505.

Figure 6:
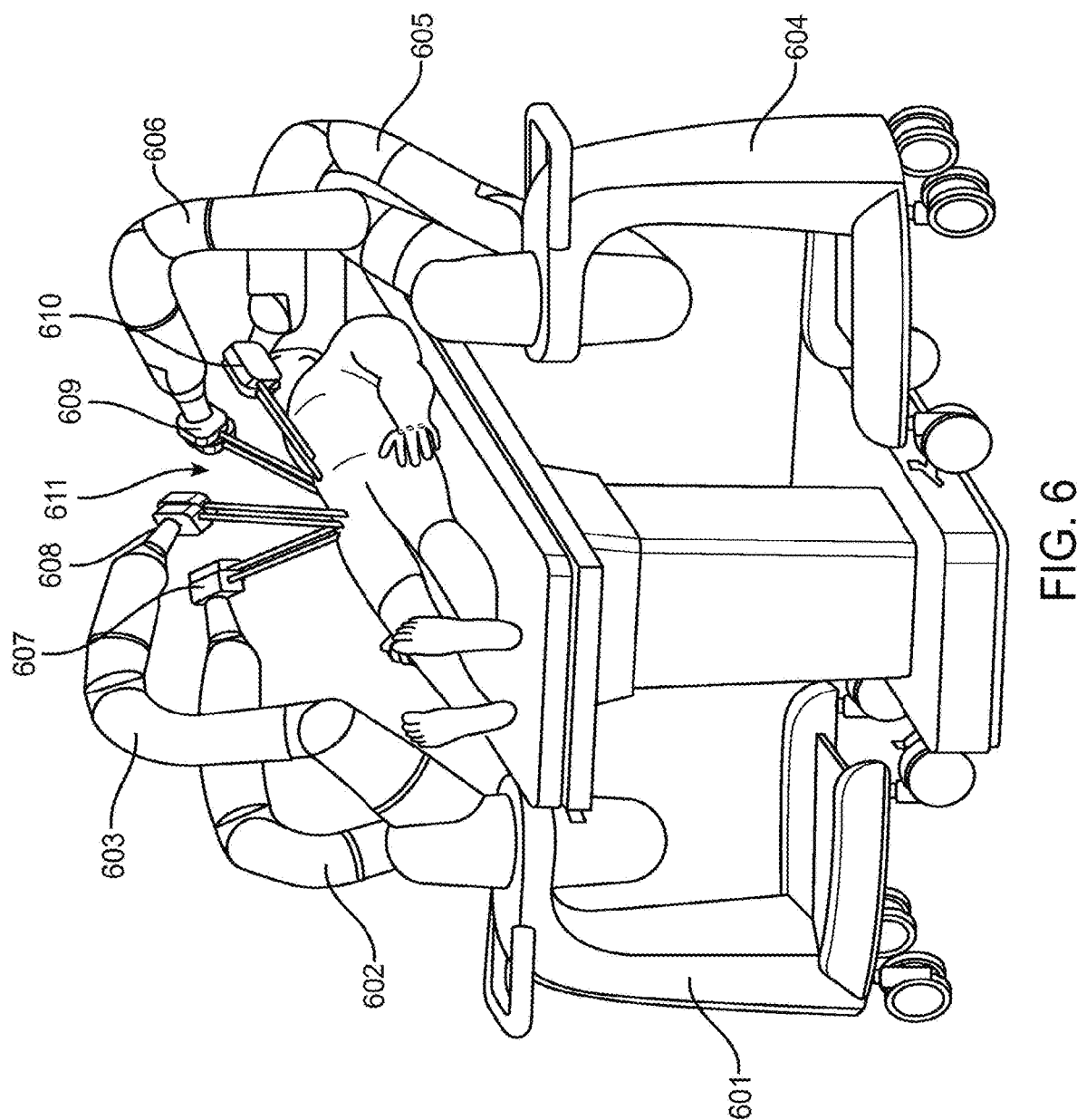

FIG. 6 illustrates an embodiment of the present invention with two sets of robotic subsystems 601 and 604, each with a pair of robotic arms 602, 603 and 605, 606 respectively. Connected through instrument interfaces at the distal end of each robotic arm are laparoscopic instruments 607, 608, 609, 610 for procedures in an individual patient 611.

Figure 7:
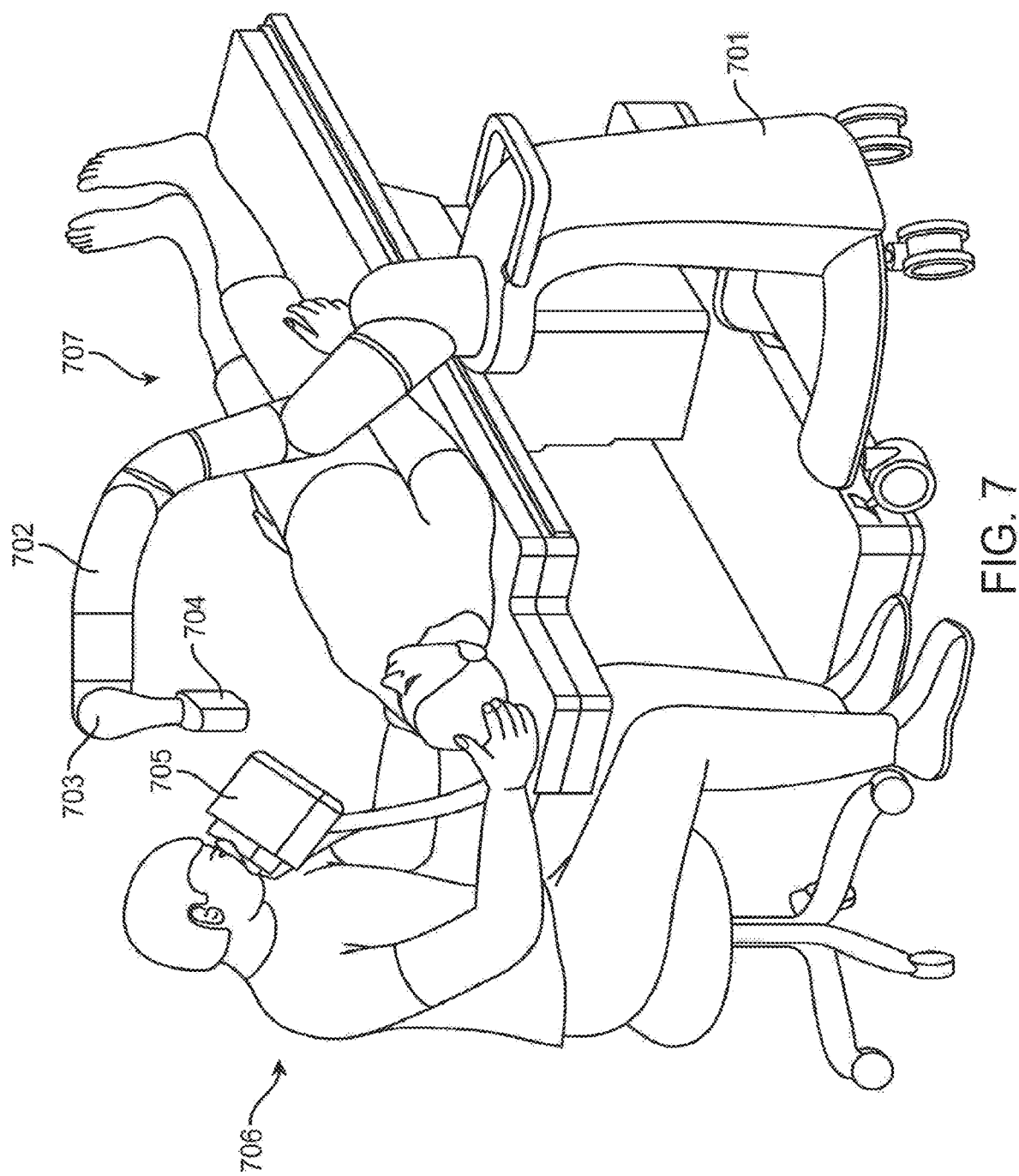
FIGS. 7 and 8 illustrate alternative embodiments of modules for the robotic surgical system of the present invention

FIG. 7 illustrates an embodiment of the present invention with a subsystem 701 with a single robotic arm 702, where a microscope tool 704 connected to the robotic arm 702 through an instrument interface 703. In some embodiments, the microscopic tool 704 may be used in conjunction with a second microscope tool 705 used by a physician 706 to aid in visualizing the operational area of a patient 707.

Figure 8:
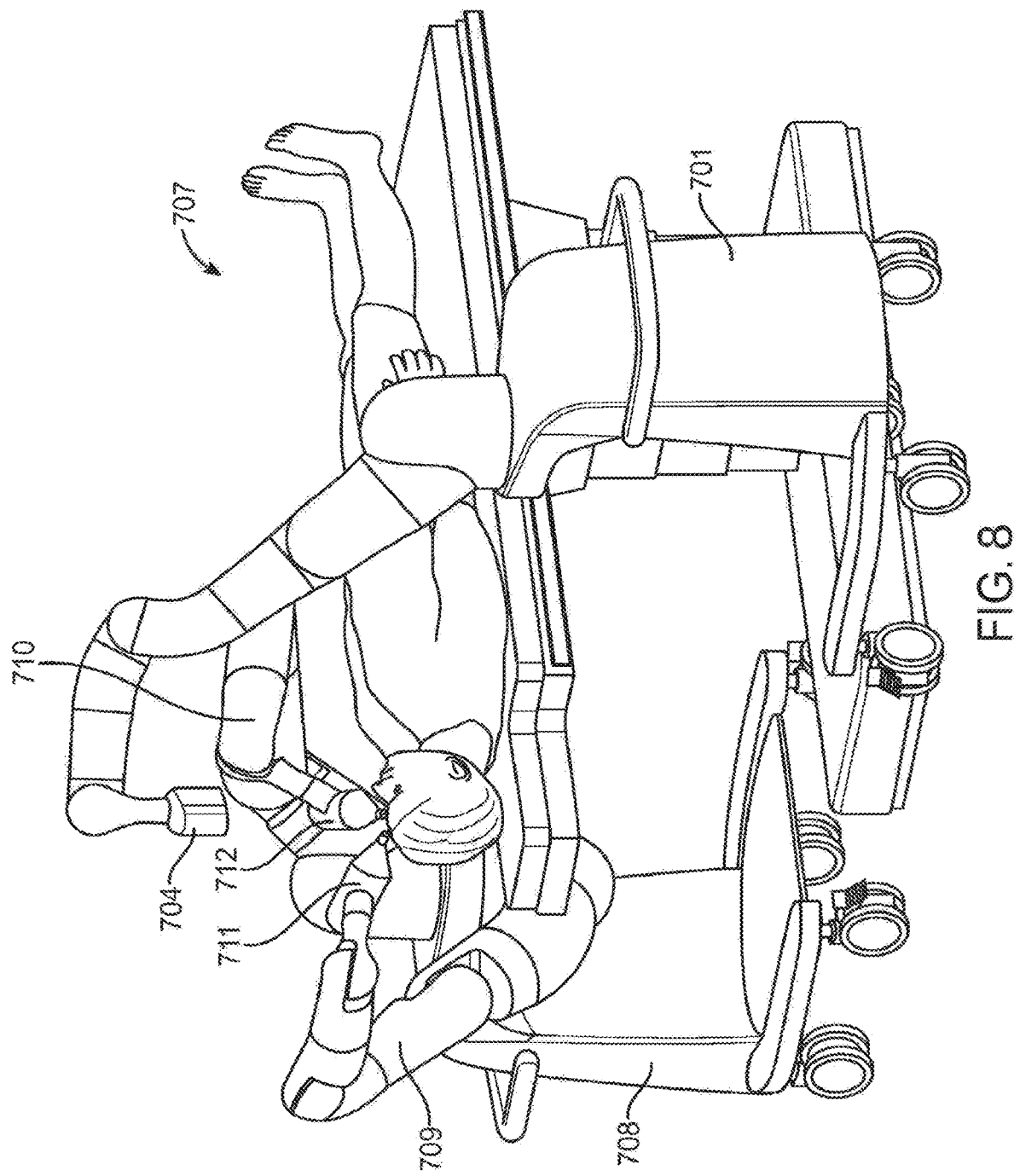

FIG. 8 illustrates an embodiment of the present invention where subsystem 701 from FIG. 7 may be used in conjunction with subsystem 708 to perform microsurgery. Subsystem 708 provides robotic arms 709 and 710, each with microsurgical tools 711 and 712 connected through instrument interfaces on each respective arm. In some embodiments, the one or more robotic arms can pick up and exchange tools at a table or other suitable holding mechanism within reach of the robotic arm. In FIG. 4A, shows the interchangeable modules are stored on the side of the cart on which the robotic arm is mounted.

Sheath and Endoscope Structure

Figure 9A:
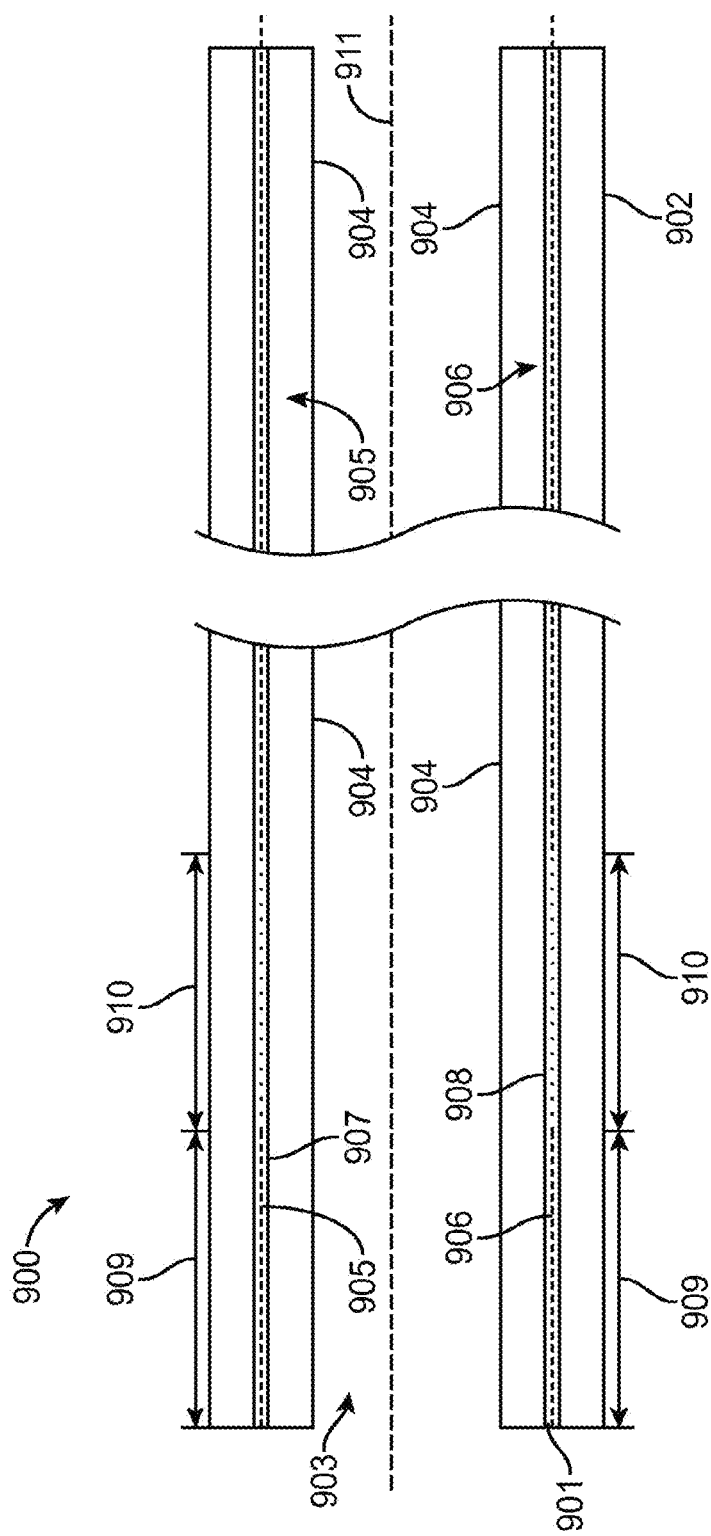
FIGS. 9A, 9B, 9C illustrate the structure of a sheath of a flexible endoscopic device, in accordance with an embodiment of the present invention.

FIGS. 9 and 10 provide details of a sheath 210 and flexible endoscope 212 in accordance with an embodiment of the present invention. FIG. 9A shows sheath 900 with distal end 901 and proximal end 902 and lumen 903 running between the two ends. Lumen 903 is preferably sized to slidingly receive a flexible endoscope (such as endoscope 1000 from FIG. 10). Sheath 900 has walls 904 with tendons 905 and 906 running inside the length of walls 904 of sheath 900. Tendons 905 and 906 slidingly pass through conduits 907 and 908 in walls 904 and terminate at distal end 901. In some embodiments, the tendons may be formed from steel. Appropriate tensioning of tendon 905 compresses distal end 901 towards conduit 907, while minimizing bending of the helixed section 910. Similarly, appropriate tensioning of tendon 906 compresses distal end 901 towards conduit 908. In some embodiments, lumen 903 may not be concentric with sheath 900.

Tendons 905 and 906 and associated conduits 907 and 908 from sheath 900 from FIG. 9A preferably do not run straight down the length of sheath 900, but helix along a helixed section 910 and then run longitudinally straight (i.e., approximately parallel to the neutral axis) along distal section 909. It will be appreciated that helixed section 910 may begin from the proximal end of distal section 909 extending proximally down sheath 910 and may terminate at any desired length for any desired or variable pitch. The length and pitch of helixed section 910 is determined based on the desired properties of sheath 900, taking into account desired flexibility of the shaft, and increased friction in the helixed section 910. Tendons 905 and 906 run approximately parallel to central axis 911 of sheath 900 when not in the helixed section, such as the proximal section of the endoscope 900.

In some embodiments, the tendon conduits may be at ninety degrees to each other (e.g., 3-, 6-, 9- and 12-o'clock). In some embodiments, the tendons may be spaced one hundred and twenty degrees from each other, e.g., three total tendons. In some embodiments, the tendons may be not be equally spaced. In some embodiments, they may be all to one side of the central lumen. In some embodiments, the tendon count may differ from three or four.

Figure 9B:
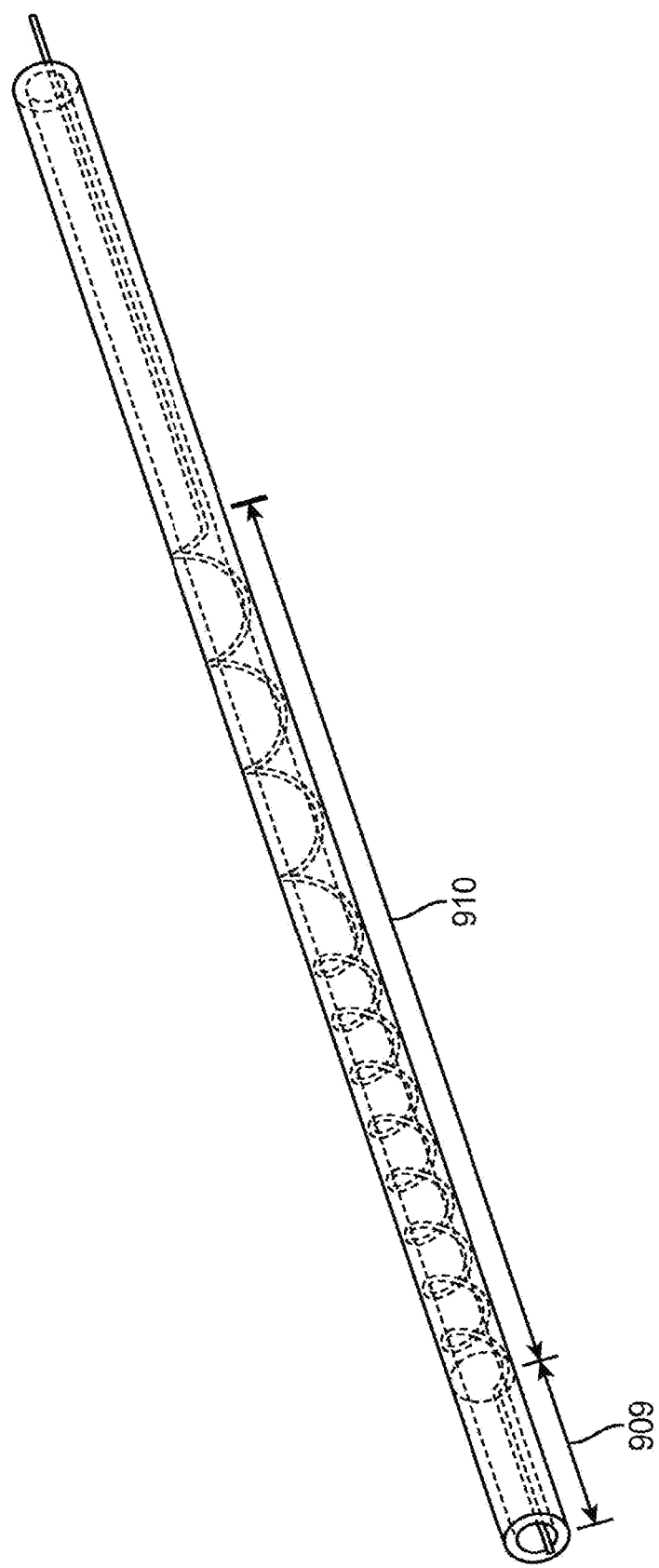
Figure 9C:
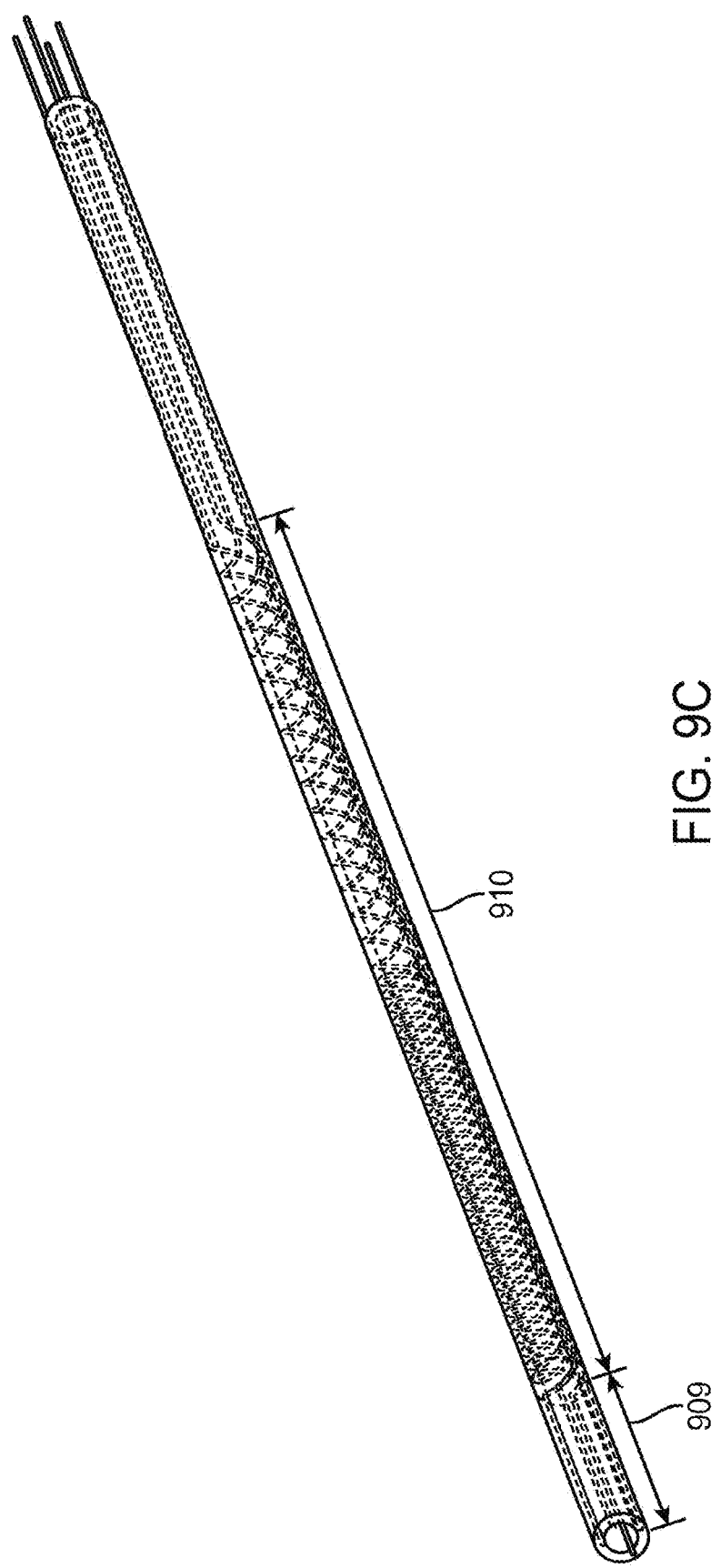

FIG. 9B shows a three-dimensional illustration of an embodiment of sheath 900 with only one tendon for the purpose of clarifying the distinction between non-helixed section 909 and a variable pitch helixed section 910. While one tendon may be used, it is preferred to use multiple tendons. FIG. 9C shows a three-dimensional illustration of an embodiment of sheath 900 with four tendons extending along distal section 909, helixed section 910 and then proximal to helixed section 910.

Figure 10A:
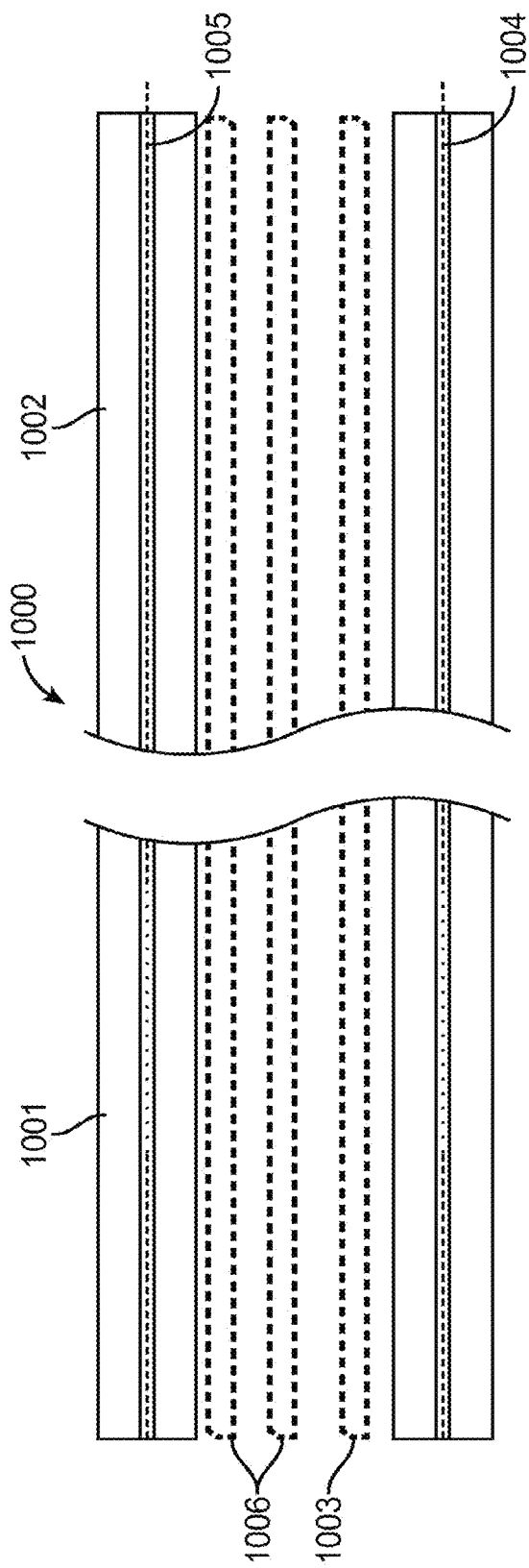
FIGS. 10A, 10B illustrate the structure of a flexible endoscopic device in accordance with an embodiment of the present invention.

FIG. 10A shows a flexible endoscope 1000 with distal end 1001 and proximal end 1002, that may be sized to slidingly reside within the sheath 900 from FIG. 9. Endoscope 1000 may include at least one working channel 1003 passing through it. Proximal end 902 of sheath 900 and proximal end 1002 of flexible endoscope 1000 are, respectively, operatively connected to modules 206 and 208 from FIG. 2 respectively. Tendons 1004 and 1005 slidingly pass through conduits 1006 and 1007 respectively in walls 1008 and terminate at distal end 1001.

Figure 10B:
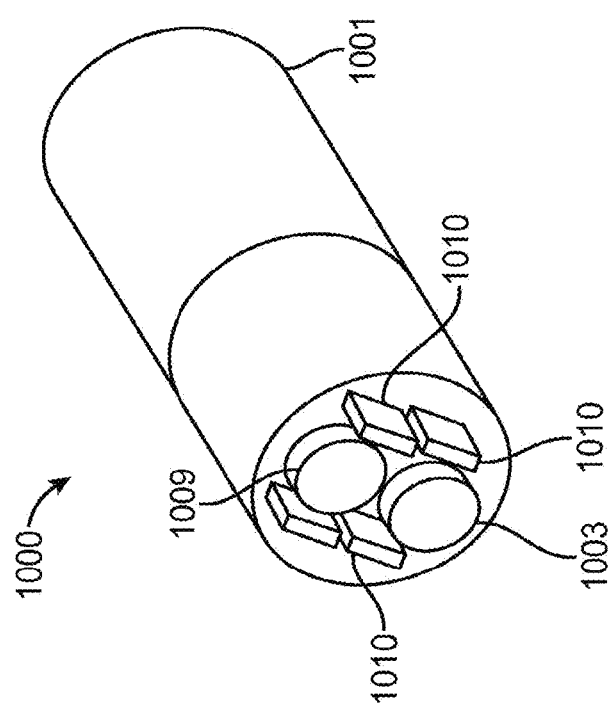

FIG. 10B shows the distal end 1001 of flexible endoscope 1000, an exemplary embodiment, that has imaging 1009 (e.g., CCD or CMOS camera, terminal end of imaging fiber bundle etc.), light sources 1010 (e.g., LED, optic fiber etc.) and may include at least one working channel opening 1003. Other channels or operating electronics 1006 may be provided along flexible endoscope 1000 to provide various known capabilities at the distal end, such as wiring to camera, insufflation, suction, electricity, fiber optics, ultrasound transducer, EM sensing, and OCT sensing.

In some embodiments, the distal end 1001 of endoscope 1000 may include a "pocket" for insertion of a tool, such as those disclosed above. In some embodiments, the pocket may include an interface for control over the tool. In some embodiments, a cable, such as an electrical or optical cable, may be present in the endoscope in order communicate with the interface.

In some embodiments, sheath 900 from FIG. 9A and flexible endoscope 1000 from FIG. 10A both, preferably, may have robotically controlled steerable distal ends. The structure of sheath 900 and flexible endoscope 1000 enabling this control is thus substantially the same for both, and thus discussion for the construction of sheath 900 will be limited to that of the sheath 900 with the understanding that the same principles apply to the structure of the flexible endoscope 1000.

Therefore, tendons 1004 and 1005 and associated conduits 1006 and 1007 from the endoscope 1000 from FIG. 10A do not run longitudinally straight (i.e., approximately parallel to the neutral axis) down the length of endoscope 1000, but helix along different portions of endoscope 1000. As with the helixed tendons and conduits in sheath 900, the helixed sections of endoscope 1000 may be determined based on the desired properties of the endoscope, taking into account desired flexibility of the shaft, and increased friction in the helixed section. Tendons 1004 and 1005 run approximately parallel to central axis of endoscope 1000 when not in the helixed section.

The purpose of the helixed section, as described more fully below, is to help isolate the bending to the distal section, while minimizing bending that occurs along the shaft proximal to the distal section. In some embodiments of the present invention, the helix pitch of the conduits in sheath 900 and endoscope 1000 may be varied along the length of the helixed section, which, as more fully described below will alter the stiffness/rigidity of the shaft.

The use of helixed conduits and helixed tendons in sheath 900 and endoscope 1000 present significant advantages over previous flexible instruments without helixed conduits, particularly when navigating non-linear pathways in anatomical structures. When navigating curved pathways, it is preferable for sheath 900 and endoscope 1000 to remain flexible over most of the lengths thereof, and to have a controllably steerable distal end section, while also minimal secondary bending of the instrument proximal to the distal bending section. In previous flexible instruments, tensioning the tendons in order to articulate the distal end resulted in unwanted bending and torqueing along the entire length of the flexible instrument, which may be referred to as "muscling" and "curve alignment" respectively.

Figure 11A:
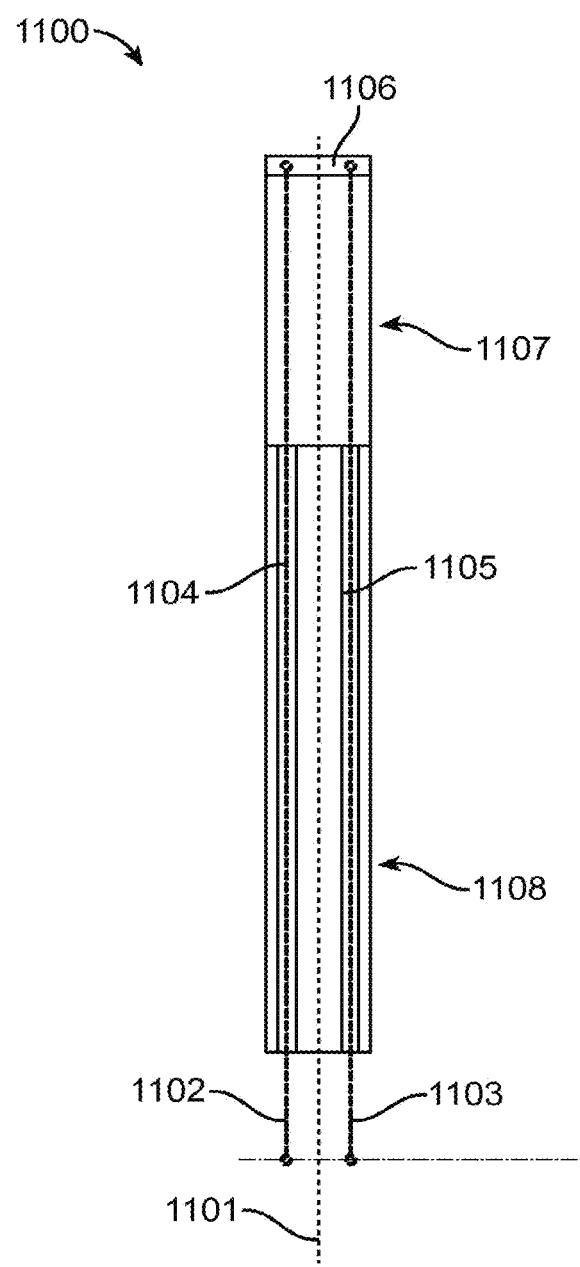
FIGS. 11A-11K illustrate muscling and curve alignment phenomena that manifest in previous flexible instruments and the improvement shown by an embodiment of the present invention.
Figure 11B:
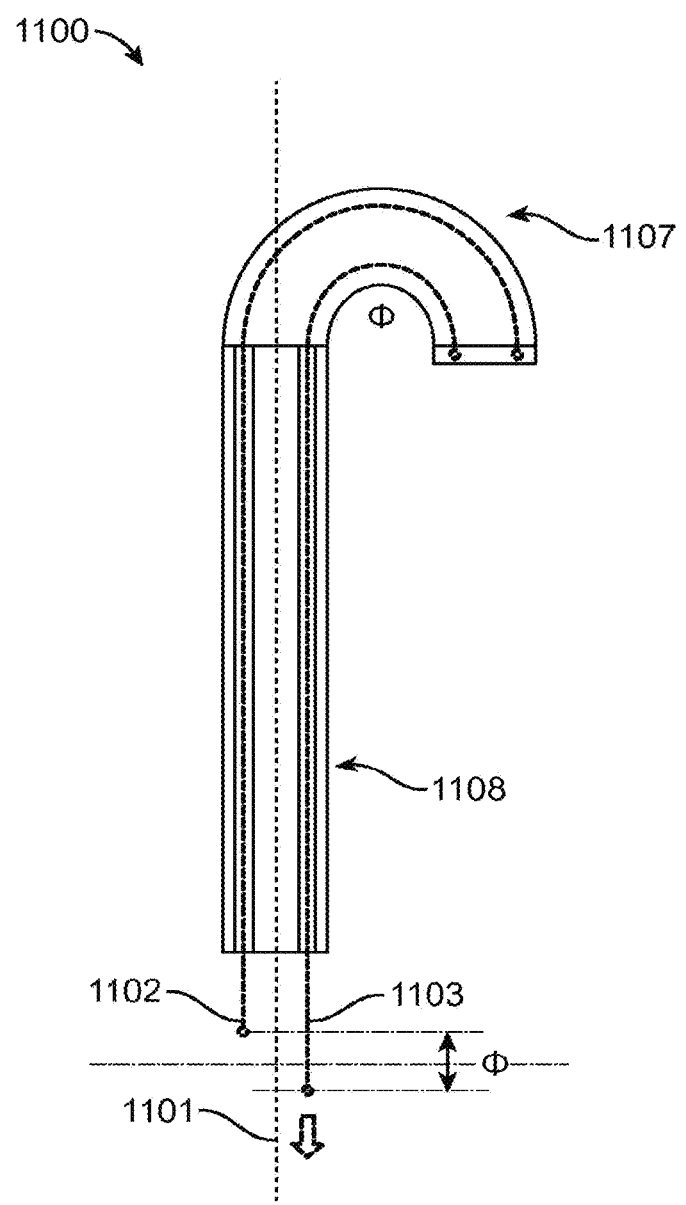
Figure 11C:
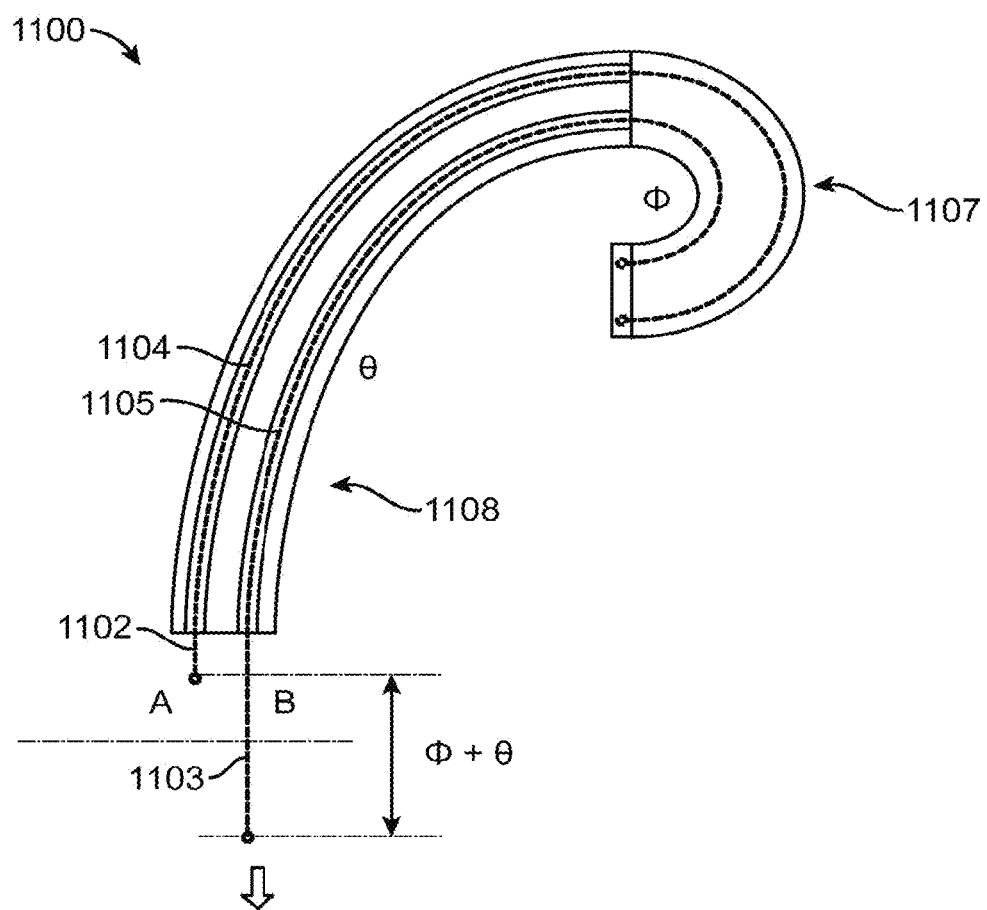

FIGS. 11A to 11C illustrates how the prior flexible instruments exhibit undesirable "muscling" phenomenon when tendons are pulled. In FIG. 11A, a previous flexible instrument 1100 may have four tendons or control wires along the length of the instrument 1100 that run approximately parallel to the neutral axis 1101. Only tendons 1102 and 1103 are shown in cross section traveling through conduits 1104 and 1105 (also known as control lumens) in the shaft wall, each of which are fixed connected to a control ring 1106 on the distal end of the instrument 1100. Instrument 1100 is intentionally designed to have a bending section 1107 and shaft 1107. In some flexible instruments, the shaft 1108 may incorporate stiffer materials, such as stiffeners.

FIG. 11B illustrates an idealized articulation of the bending section 1107. By pulling or exerting tension on tendon 1103, articulation of only the distal bending section 1107 results an amount represented by $\phi$, where the length difference at the proximal ends of tendons 1102 and 1103 would be a $f(\phi)$. In contrast, the shaft 1108 remains straight along the neutral axis 1101. This is achieved by having a proximal region 1108 of a significantly higher stiffness than the distal region of 1107.

FIG. 11C illustrates the real world result from tensioning tendon 1103. As shown in FIG. 11C, pulling tendon 1103 results in compressive forces along the entire length of the shaft as the tension is non-localized. In an idealized situation, were tendon 1103 along the neutral axis 1101, the entire compressive load would transmit equally down the central axis and most or all bending would occur at the bending section 1107. However, where the tendon 1103 runs along the periphery of the shaft 1108, such as in instrument 1100, the axial load is transferred off the neutral axis 1101 in the same radial orientation of the neutral axis which creates a cumulative moment along the neutral axis. This causes the shaft 1108 to bend (depicted as $\theta$), where the bend in the shaft 1108 will be in the same direction as the bend in the bending section 1107. The length along conduit 1104 and conduit 1105 must change as the instrument 1100 and distal bend section 1107 bend. The amount tendons 1102 and 1103 extend from the proximal end is $f(\phi,\theta)$, as tendon 1103 will need to shorten and tendon 1102 will need to lengthen. This phenomenon, where the shaft 1107 and distal bending section 1108 bend from pulling tendon 1103, is referred to as "muscling."

Figure 11D:
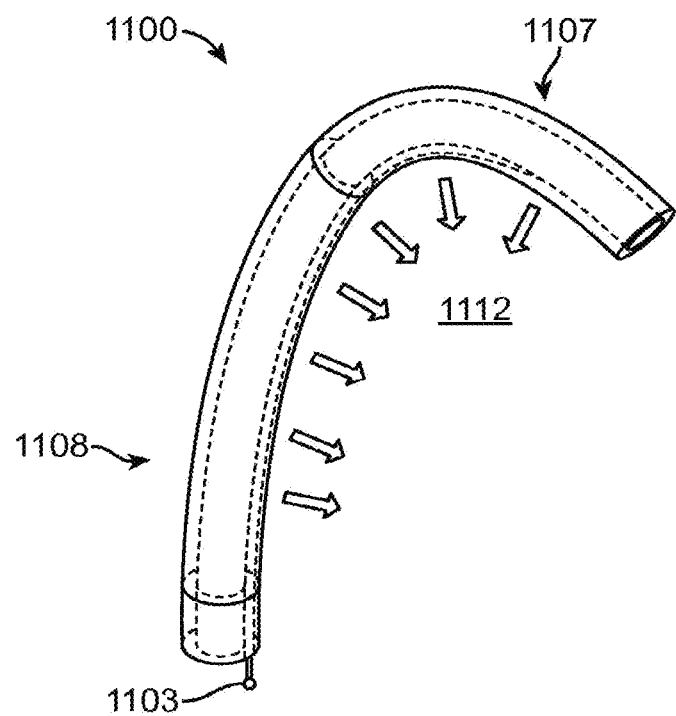
Figure 11E:
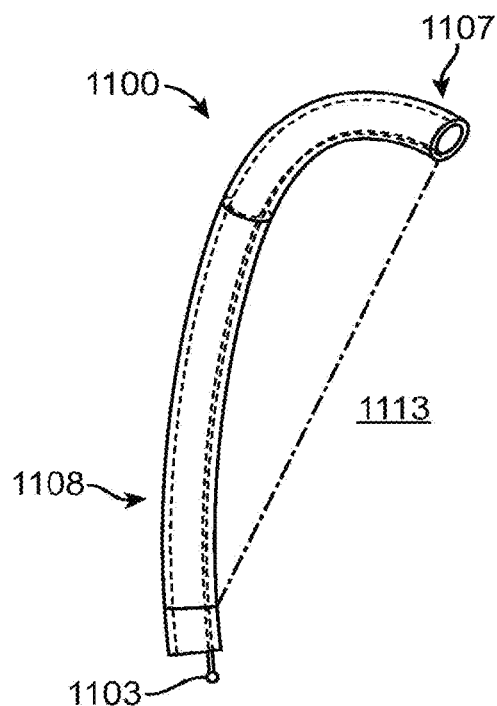

FIG. 11D illustrates the forces that contribute to muscling in three-dimensions. As shown by FIG. 11D, tensioning tendon 1103 along instrument 1100 causes the tendon 1103 to directionally exert forces 1112 towards one side of the instrument. The direction of forces 1112 reflect that the tension in tendon 1103 causes the tendon to seek to follow a straight line from the tip of the distal bending section 1107 to the base of the shaft 1108, i.e., the lowest energy state as represented by the dotted line 1113 in FIG. 11E. As will be appreciated, if the shaft 1108 is rigid (i.e., not susceptible to bending under the applicable forces), only the distal bending section 1107 will bend. However, in many applications it is not desirable to make the shaft rigidity sufficiently different from the distal end to adequately minimize the muscling phenomenon.

Figure 11F:
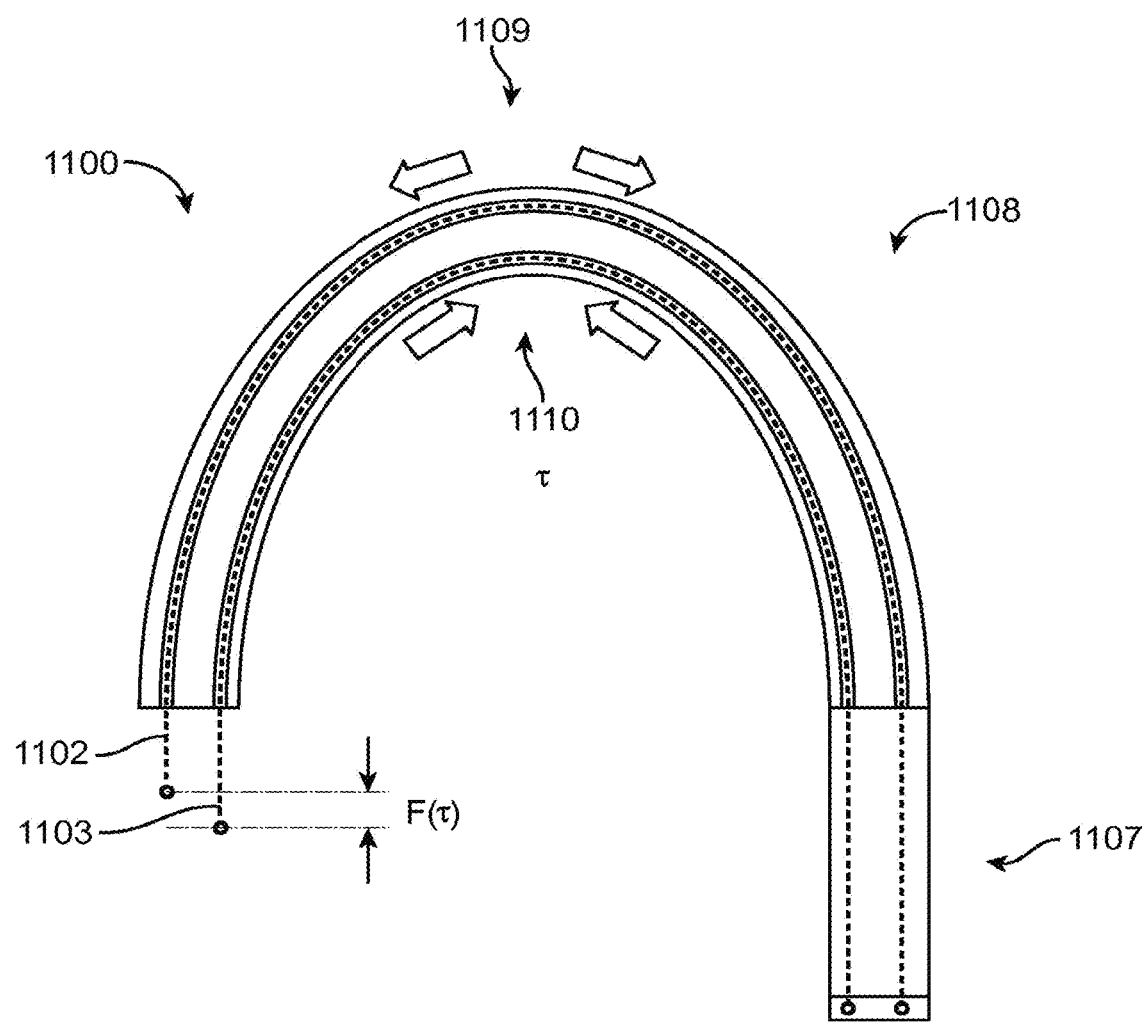

FIGS. 11F to 11J illustrate how previous flexible instruments suffer from curve alignment phenomenon during use in non-linear pathways. FIG. 11F shows a previous flexible instrument 1100 at rest within a non-linear path, represented by having a bend r along the shaft 1108 of instrument 1100. For example, this may result from the instrument navigating past a bend in the bronchial lumens. Due to the non-linear bend, tendons 1102 and 1103 in instrument 1100 need to lengthen or shorten at the proximal end by a length to accommodate the non-linear bend, which length is represented by $F(\tau)$. Extension and compressive forces exist on the lumens/conduits at the top and bottom of the bend, as depicted by arrows 1109 (extension forces) and 1110 (compressive forces) respectively. These forces exist because the distance along the top of the bend is longer than the neutral axis, and the distance along the inside of the bend is shorter than the neutral axis.

Figure 11G:
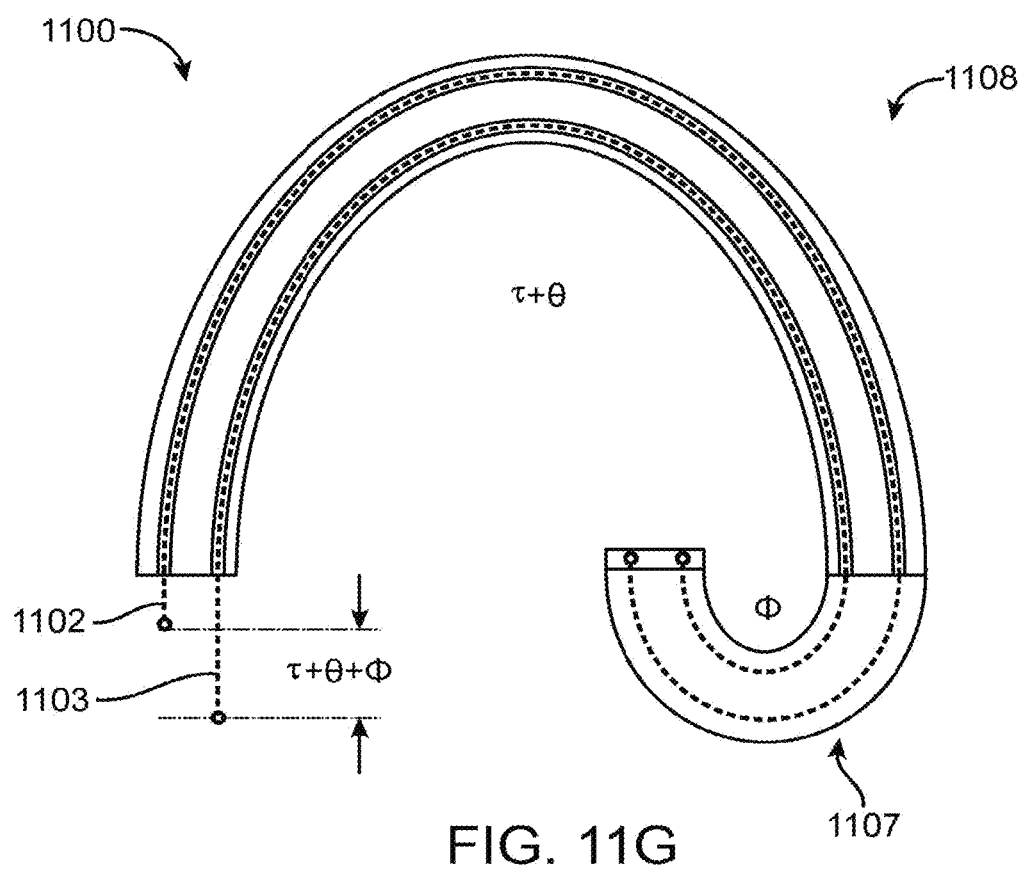

FIG. 11G illustrates the mechanics of articulating the distal bending section 1107 of the instrument 1100 in the same direction as bend r, where one would pull tendon 1103. This results in compressive forces along the length of the flexible instrument (as previously described), and tendon 1103 also exerts downward forces against the non-linear conduit through which it passes, which applies an additive compression in the shaft 1108 previously compressed by the anatomical tortuosity. Since these compressive leads are additive, the shaft 1108 will further bend in the same direction as the distal bending section 1107. The additional compressive force along the non-linear conduit is highly undesirable because: (i) it forces the flexible instrument against the anatomy causing potential injury; (ii) potential for injury distracts the operator because he/she has to constantly monitor what the shaft is doing, when he/she should be able to "assume" the anatomy is governing the profile of the instrument shaft; (iii) it is an inefficient way to bend the instrument, (iv) it is desired to isolate bending at the distal section to aid in predictability and controllability (i.e., ideal instrument will have bending section that bends as commanded and is not a function of the anatomical non-linear path), and (v) it forces a user to pull on a tendon 1103 an unpredictable additional length ($\phi+\theta+\tau$).

Figure 11H:
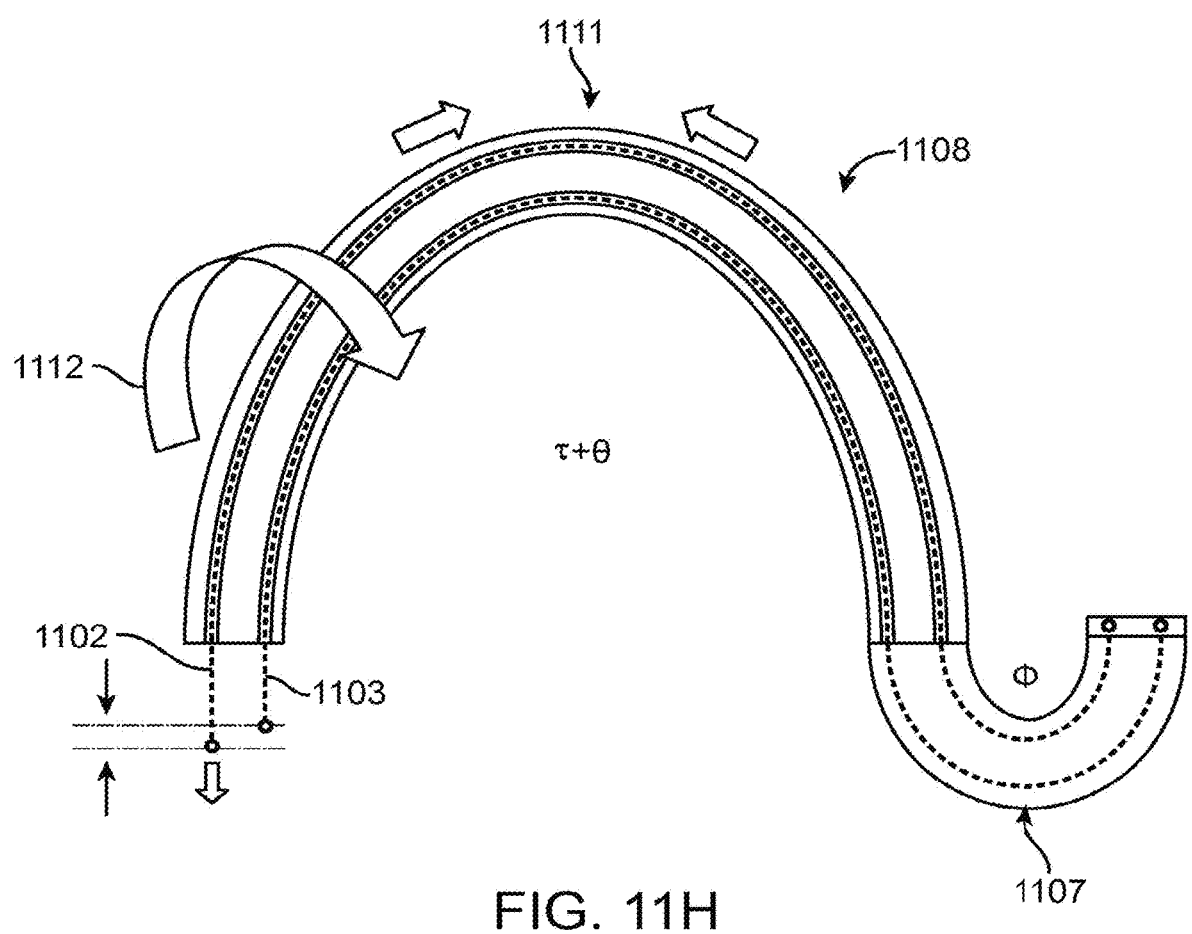
Figure 11I:
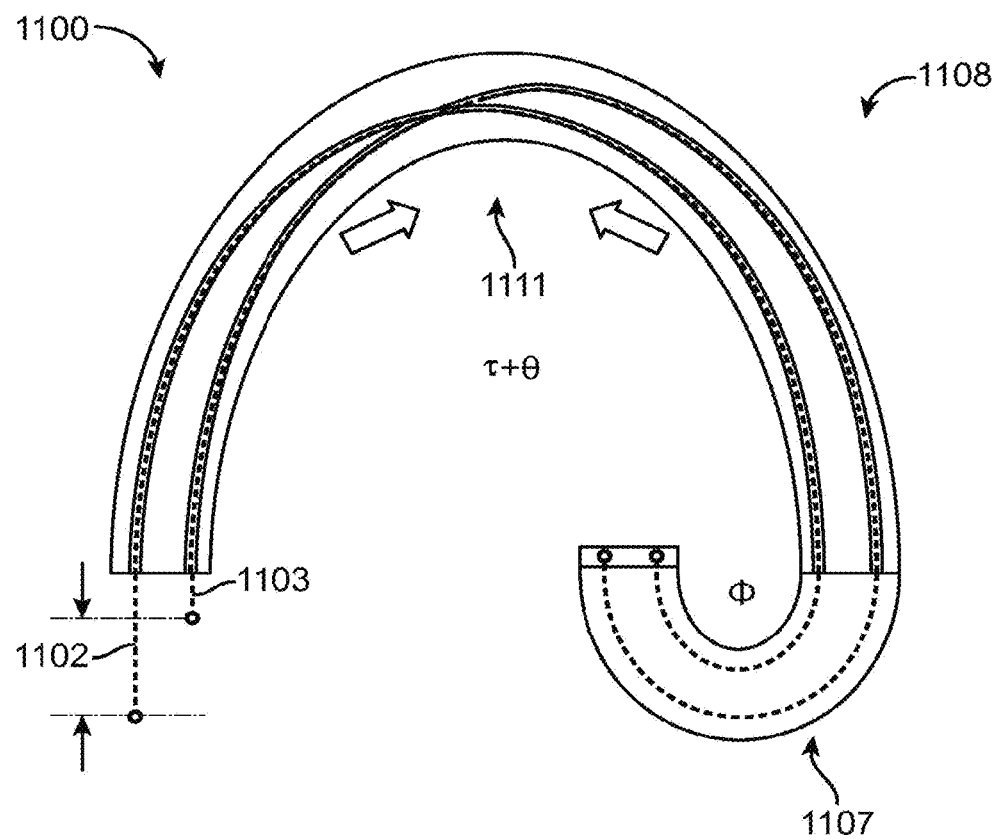
Figures 11J, 11K:
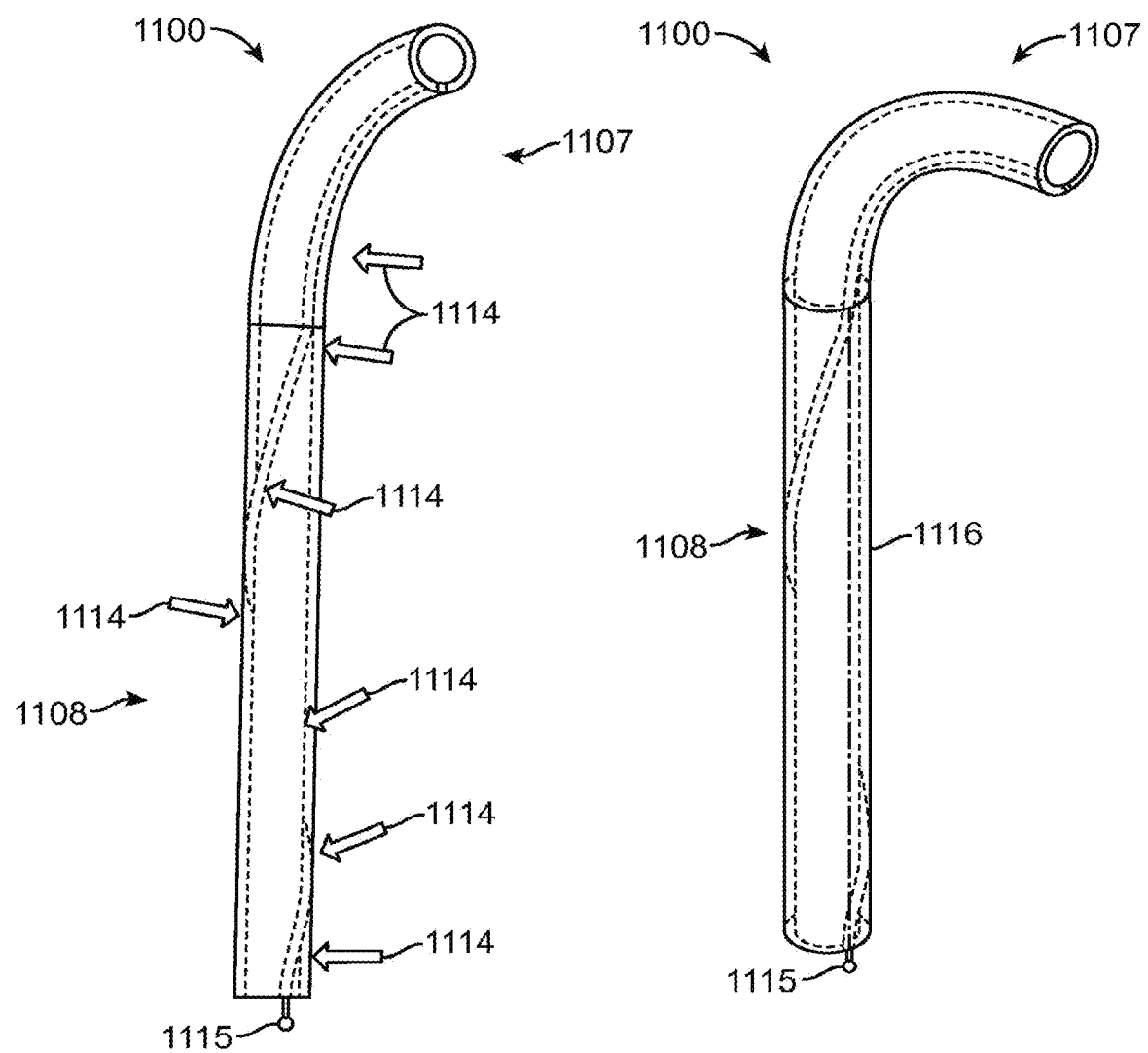

FIG. 11H illustrates a scenario where one desires to articulate the distal end opposite to bend ti, requiring pulling tendon 1102. Pulling tendon 1102 applies a compressive load 1111 along the top of the curve, which is in contrast to the extension loads for the bend in its resting state as shown in FIG. 11D. Tendons 1102 will attempt to return to its lowest energy state, i.e., where the compressive load 1111 rests on the inside of the bend $\tau$, and cause the shaft 1108 to rotate in the direction of the arrow 1112 so that the tendon 1102 rests on the inside of the bend τ. As shown in FIG. 11J, the rotation 1112 from tension on tendon 1102 moves the compressive load 1111 to return to the inside of the bend and causes the distal bending section 1107 to curl back in the direction of bend τ, resulting in articulation opposite to that intended. The tension on tendon 1102, and the ensuing rotation 1112, in practice returns instrument 1100 to the same state as in FIG. 11G. The phenomenon where the distal end articulation curves back towards bend τ is known as "curve alignment." It will be appreciated that curve alignment results from the same forces that cause muscling, wherein those forces result in undesirable lateral motion in the case of muscling and undesirable rotational motion in the case of curve alignment. It is noted that the discussions of the theory of muscling and curve alignment is provided not by way of limitation, and embodiments of the present invention are not in any way limited by this explanation.

The preferred embodiment disclosed in FIGS. 9 and 10 substantially resolves the muscling and curve alignment phenomena through the provision of helixed section 910. As shown in FIG. 11K, helixing the control lumens around instrument 1100, such as in helixed section 910 from FIGS. 9B and 9C, radially distributes compressive loads 1114 from a single tendon 1115 around instrument 1100. Because a tensioned tendon 1115 symmetrically transmits the compressive load 1114 in multiple directions around the neutral axis, the bending moments imposed on the shaft are also symmetrically distributed around the longitudinal axis of the shaft, which counterbalance and offset opposing compressive and tensile forces. The distribution of the bending moments results in minimal net bending and rotational forces, creating a lowest energy state that is longitudinally parallel to the neutral axis, as represented by the dotted line 1116. This eliminates or substantially reduces the muscling and curve alignment phenomena.

In some embodiments, the pitch of helixing can be varied to affect friction and the stiffness of the helixed section. For example, the helixed section 910 may be shorter to allow for a larger non-helixed section 909, resulting in a larger articulating section and possibly less friction.

Helical control lumens, however, create several trade-offs. Helical control lumens still do not prevent buckling from tension in the tendons. Additionally, while muscling is greatly reduced, "spiraling"—the curving of the shaft into a spiral, spring-like pattern due to tension in the tendons—is very common. Moreover, helical control lumens requires compensation for additional frictional forces as the tendon travels through the lumen for longer distances.

Figure 12:
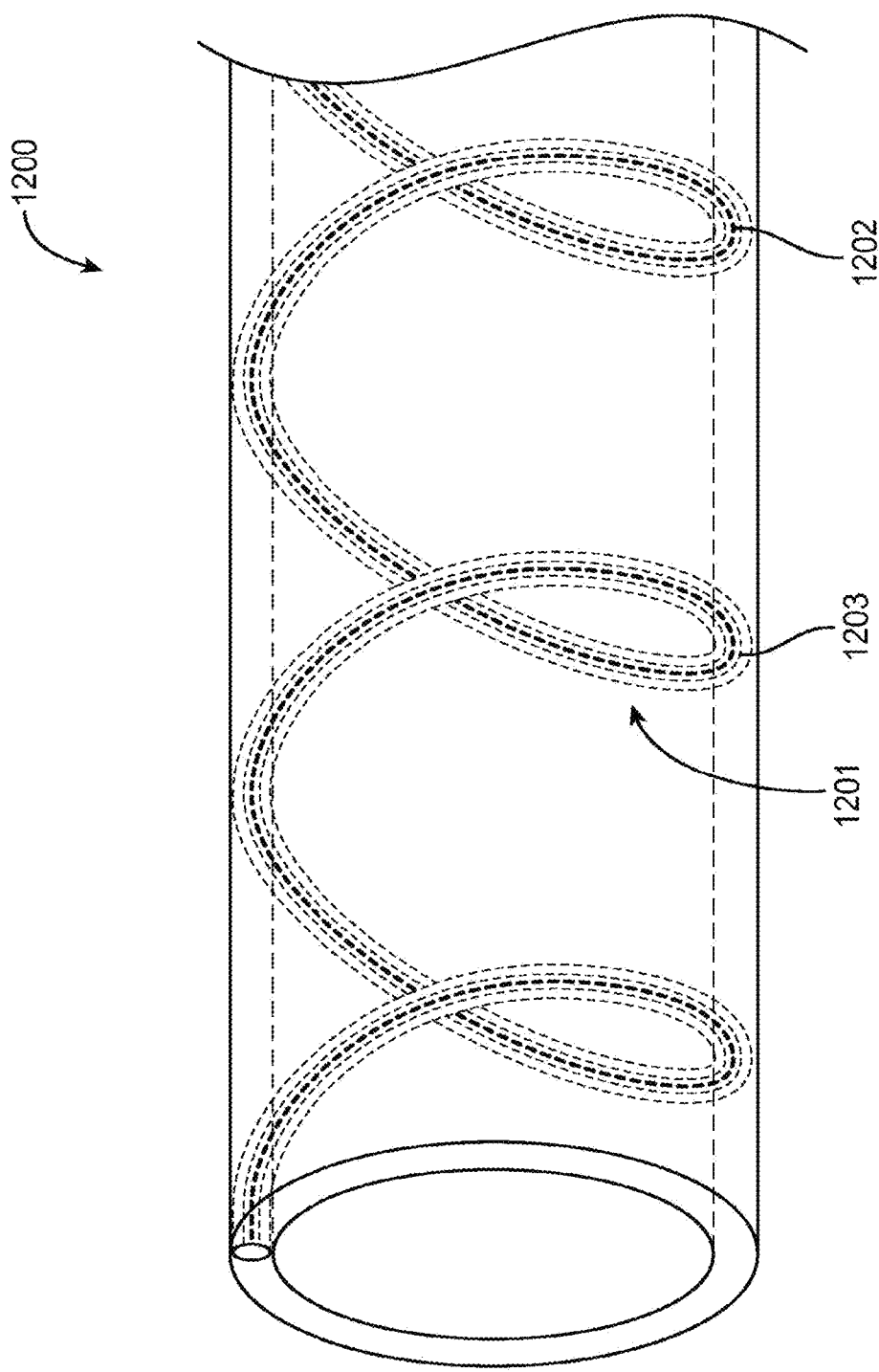
FIG. 12 illustrates the structure of flexible endoscopic device with an axially stiff tube within a lumen, in accordance with an embodiment of the present invention.

FIG. 12 illustrates the structure of a flexible endoscopic device with an axially stiff tube within a lumen, in accordance with an embodiment of the present invention. In FIG. 12, a section of an endoscopic device has a single lumen 1201 with a pull wire 1202 wrapped in a helical pattern around the shaft 1200. Inside the lumen, an axially stiff tube 1203 "floats" around the pull wire 1202 and within the lumen 1201. Anchored at the beginning and end of the helical portion of the shaft 1200, the floating tube 1203 extends and compresses in response to tension in pull wire 1202 and external tortuosity, relieving the walls of lumen 1201 from the extension and compression forces. In some embodiments, the tube 1203 may be anchored by pull rings at the beginning and end of the lumen. Alternatively, tube 1203 may be anchored using solder, welding, gluing, bonding, or fusing methods to the beginning and end of the lumen. In some embodiments, geometric engagement, such as flared geometries, may be used to anchor tube 1203. In various embodiments, the tube 1203 may be formed from hypodermic tubes, coil pipes, Bowden cables, torque tubes, stainless steel tubes, or nitinol tubes.

The embodiment in FIG. 12 may be constructed by fixedly attaching the tubes to a distal end piece and proximal end piece and collectively twisting the tubes by rotating either or both end pieces. In this embodiment, the rotation of the end piece(s) ensures that the tubes are helixed in the same pitch, manner, and orientation. After rotation, the end pieces may be fixedly attached to the lumen to prevent further rotation and restrict changes to the pitch of the helixing.

Figure 13:
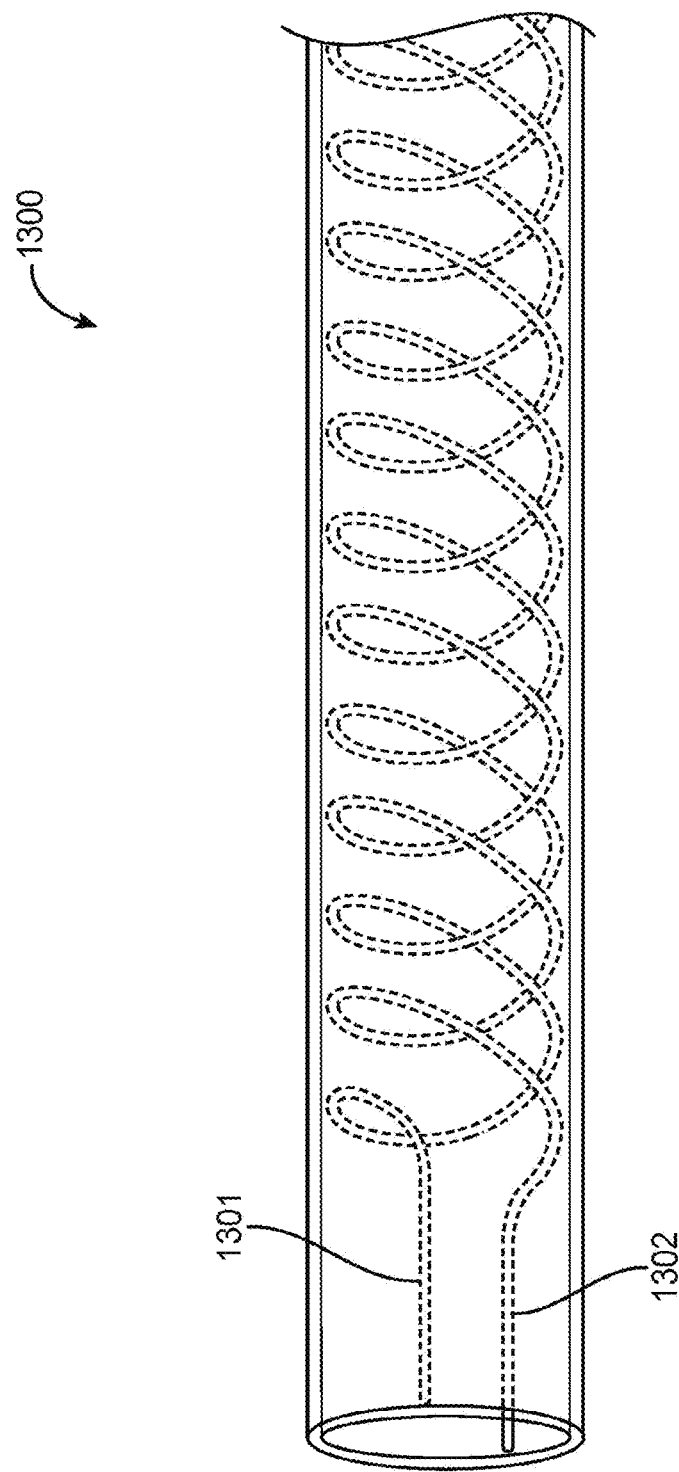
FIG. 13 illustrates the structure of a helical pattern within a lumen of a flexible endoscopic device, in accordance with an embodiment of the present invention.

FIG. 13 illustrates the structure of a helical pattern within a lumen of a flexible endoscopic device, in accordance with an embodiment of the present invention. In FIG. 13, lumen 1300 contains structures 1301 and 1302 that form a helical or spiraled pattern along its walls. In preferred embodiments, the structures are formed from materials that are axially stiff and tube-like in shape. In some embodiments, the structures may be formed from hypodermic tubes ("hypo tube"), coil pipes, or torque tubes. As shown by structures 1301 and 1302, the structures may have different starting points along the walls of lumen 1300. The materials, composition, and characteristics of structures 1301 and 1302 may also be selected and configured for desired stiffness and length. The pitch of the helical pattern formed by structures 1301 and 1302 may also be configured for a desired stiffness and flexibility of lumen 1300. In some embodiments, lumen 1300 may be the main central lumen of a flexible endoscope, such as endoscope 1000 from FIG. 10.

Sheath & Endoscope Manufacture

In the preferred embodiment, the sheath and endoscope devices are constructed using steerable catheter construction methodologies. Traditionally, steerable catheters have been manufactured by braiding wires or fibers, i.e., braid wire, around a process mandrel in a braiding machine, i.e., braider. During manufacture, a process mandrel would be typically inserted into a feed tube of a braider that was coupled to a braid cone support tube and braid cone holder. Using a puller with a tread, the process mandrel would be advanced through the feed tube. As the process mandrel progressed, it would eventually emerge through a center hole in a nose cone. The nose cone provided a round, smooth shape on which the braid wire from the surrounding horn gears may easily slide around the mandrel during the braiding process. The nose cone was typically held in a position that was fixed axially and radially relative to the braid cone holder using a set screw keyed to the braid cone holder. As the process mandrel was pulled through the nose cone, the horn gears translate and rotate around the mandrel to braid the braid wire around the mandrel in a pre-determined pattern and density.

In traditional steerable catheter construction, smaller supplemental mandrels are passed through the center of the horn gears for braiding onto the main process mandrel. The supplemental mandrels, sometimes constructed from Teflon-coated polyimide, may be braided onto the main process mandrel as it is pulled through the nose cone. Alternatively, it is known in the art that the supplemental mandrels may be passed through small holes in the nose cone that surround the center hole. As the main process mandrel is pulled through the nose cone, the smaller, supplemental mandrels may be braided to the main process mandrel as they are pulled from the nose cone.

In order to hold the supplemental mandrels in place, a second layer of braid wire is typically laid onto the main process mandrel after applying the supplemental mandrels.

Upon completion of the braided process, a polymer coating or jacket may be sheathed, heated, and bonded to the braiding composite. After bonding, the mandrels are typically removed from the braided composite to create a central lumen (main process mandrel) for camera and light tools, and several control lumens (supplemental mandrels) for steering control. This method of manufacture results in endoscopes with control lumens that are longitudinally parallel to the neutral axis. As discussed earlier, catheter-like endoscopes with tension on tendons in longitudinally parallel lumens exhibit muscling and curve alignment phenomena.

Figure 14:
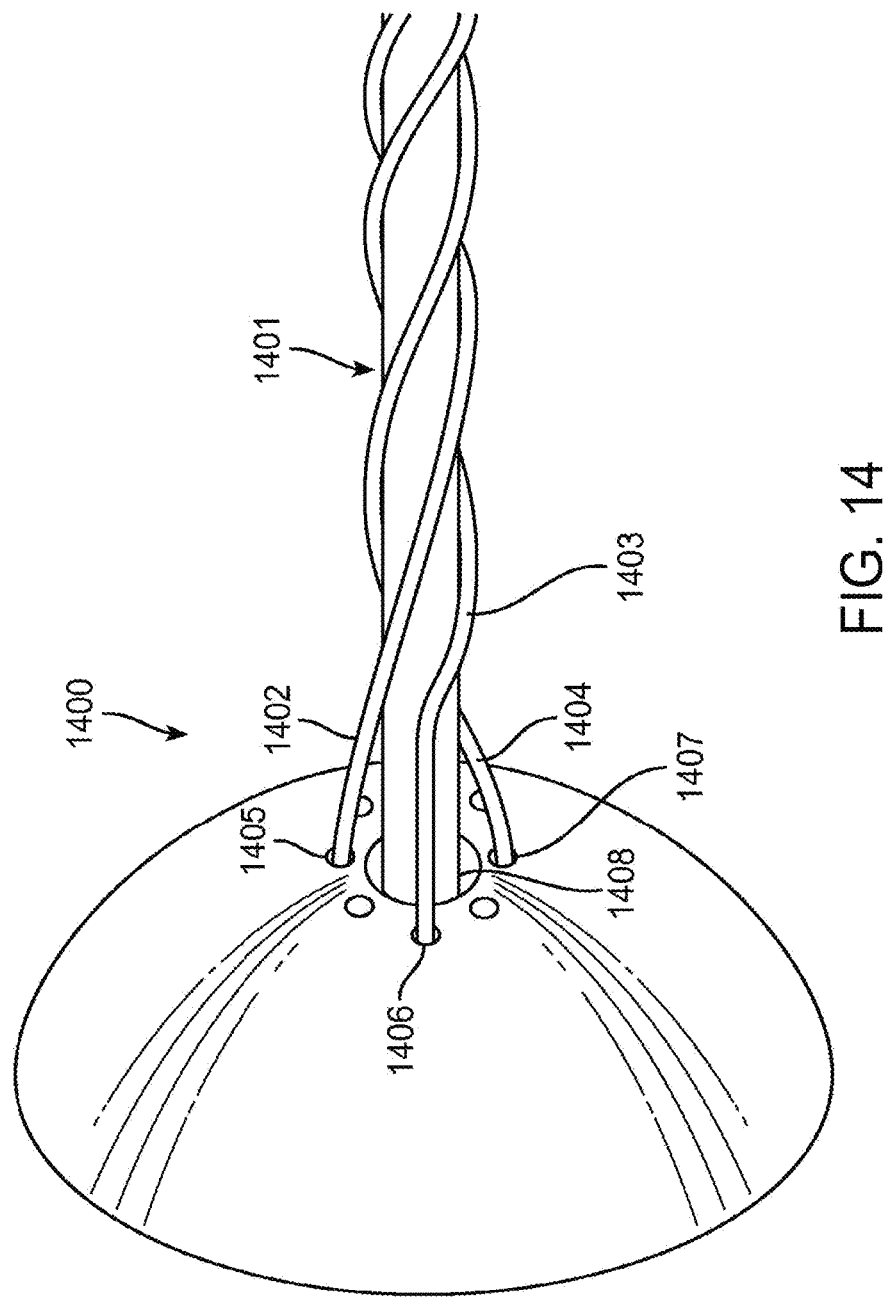
FIG. 14 illustrates a specialized nose cone for manufacturing flexible endoscopic devices, in accordance with an embodiment of the present invention.

Accordingly, specialized hardware is required for the braiding process in order to manufacture catheter-like endoscopes with helixed control lumens. One such piece of hardware is a specialized rotating nose cone that is fixedly coupled to a rotating feed tube, or "hypotube" in some embodiments. FIG. 14 illustrates a specialized nose cone for manufacturing helical lumens in a flexible sheath and/or endoscope, in accordance with an embodiment of the present invention. Rotating the nose cone 1400 at the same time that the main process mandrel 1401 is pulled through the nose cone 1400 allows for supplemental mandrels 1402, 1403, and 1404 to be applied in a helical pattern around the mandrel 1401 through supplemental holes 1405, 1406, and 1407 respectively that surround the center hole 1408, similar to how the horn gears braid the braid wire around the main process mandrel 1401.

Figure 15:
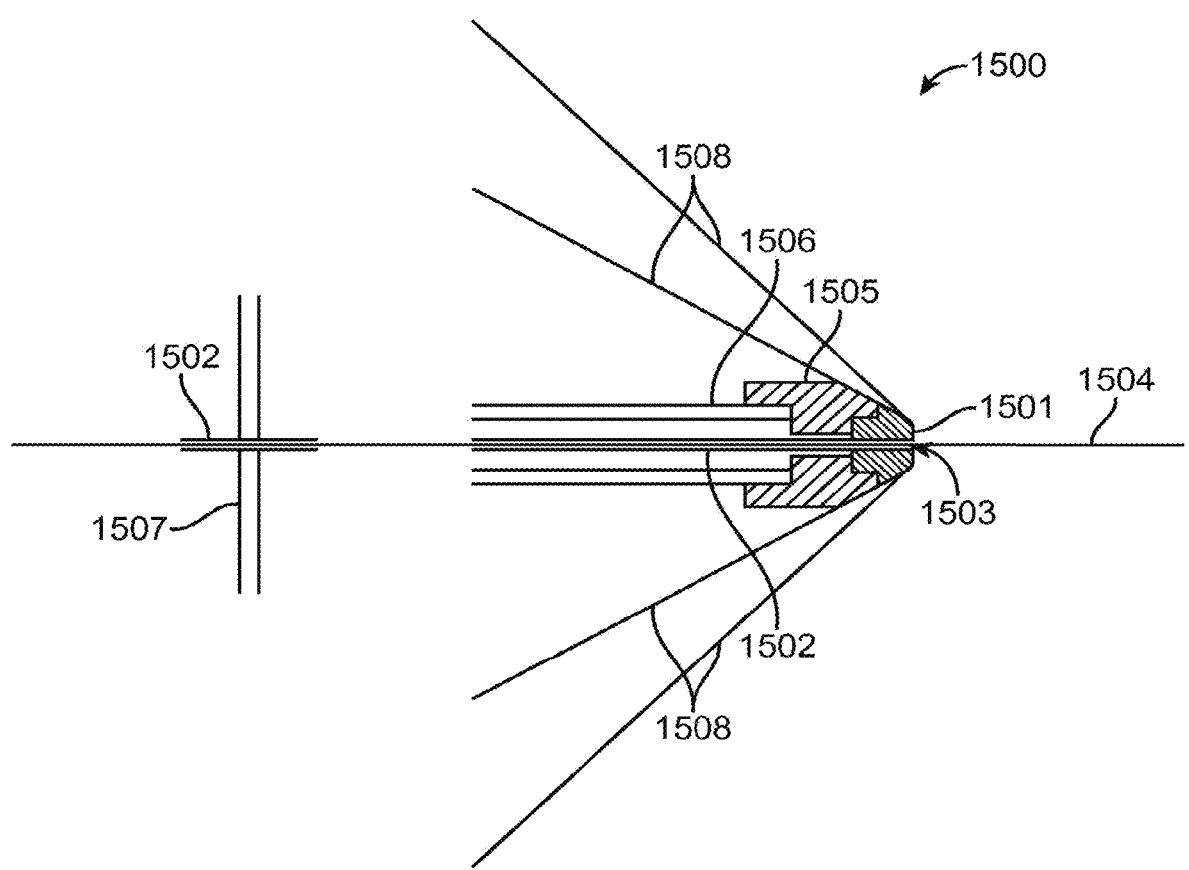
FIG. 15 illustrates a system for manufacturing a flexible endoscopic device, in accordance with an embodiment of the present invention.

FIG. 15 illustrates a system for manufacturing a flexible sheath and endoscope in accordance with an embodiment of the present invention. In system 1500, the nose cone 1501 may be fixedly coupled to a rotating feed tube 1502 using a set screw that holds the nose cone 1501 in a fixed position relative to the feed tube 1502. The center hole 1503 of the nose cone 1501 may be aligned with the rotating feed tube 1502 in order to smoothly pull the main process mandrel 1304 through both structures. In contrast, traditional systems used a set screw to fixed couple the nose cone 1501 to the braid cone support holder 1505. In some embodiments, the rotating feed tube 1502 has an outside diameter less than the interior diameter of the braid cone support tube 1506, also known as a mandrel guide tube, and an interior diameter larger than the circumferential space of the center hole 1503 of the nose cone 1501. The rotating feed tube 1502 may generally be large enough for the main process mandrel 1504 and the supplemental mandrels to be passed through to the nose cone 1501. In some embodiments, the rotating feed tube 1502 is long enough to pass through the center of the horn gears of the braider. In some embodiments, the rotating feed tube 1502 is attached to a mechanism that may hold bobbins of material for the supplemental mandrels that will be passed through the feed tube 1502 to supplemental holes around the nose cone 1501.

In some embodiments, the feed tube 1502 may be attached to a drive mechanism that controls the rate of rotation of the feed tube 1502 and thus the rotation of the nose cone 1501. In some embodiments, the drive mechanism may be a rotating gear 1507. As the braider is braiding the braid wires 1508 around the main process mandrel 1504, the drive mechanism is either geared to the braider itself or independently controlled to vary or hold constant the rate of rotation of the rotating feed tube 1502 and thus the rate of rotation of the nose cone 1501. The rate of rotation and the rate of braiding will govern the pitch of the supplemental mandrels on the main process mandrel 1504. As discussed earlier, this may affect the flexibility, stiffness, and "pushability" of the device.

In another embodiment, varying the circumferential orientation of the pull lumens may change the stiffness of the helixed section of the endoscope. In manufacture, this is achieved by altering the pitch of the supplemental, spiraling mandrels. As the pitch (i.e., the angle off the longitudinal axis) of the mandrels decreases, the bending stiffness of the braided composite increases. Conversely, as the pitch of the supplemental mandrels increases, the bending stiffness decreases. As shown in FIG. 9B, in some embodiments, the pitch of the supplemental mandrels may be varied within the helixed portion (910). In those embodiments, the bending stiffness of the braided composite may vary even within the helixed portion.

During the braiding process, the braiding machine may be stopped to make alterations to the braided composite. In some embodiments, one alteration may be the addition of straight wires or reinforcement rods. Reinforcement rods may significantly increase the buckling, axial and bending stiffness of a braided laminated composite. Reinforcement rods may be particularly helpful for longer endoscopes which may require specialized anti-buckling construction or manual assistance to reduce the buckling of the device so that it may be inserted into a patient. In some embodiments, the braiding machine may be configured to selectively braid reinforcement rods that may be pulled from holes in the nose cone onto the process mandrel, where the reinforcement rods are captured and held in place by the braid wire. The absence of reinforcement rods in the distal region of the resulting endoscope preserves the device's flexibility in the distal end while increasing the stiffness in the proximal region. This combination of properties makes the resulting endoscope easier for a physician to guide, insert, and push the device into an endolumenal cavity of a patient.

Applying supplemental mandrels onto a main process mandrel using holes in a rotating nose cone provides a number of manufacturing advantages. By using holes in the nose cone, the mandrels are not pushed from the horn gears. Pushing mandrels from the center of the individual horn gears, which are also responsible for weaving the braid wire, results in the mandrels being interwoven with the braid wire, which locks the resulting braid matrix in place longitudinally. This form of construction, known as "zero degree construction," limits the ability of the manufacturer to adjust the braid matrix for desirable flexibility or hoop strength. In zero degree construction, the supplemental mandrel is necessarily confined in an "over-under manner" by the braid, resulting in all clockwise braided braid wire being woven "over" the supplemental mandrels, while all counter-clockwise braided braid wire is woven "under" the supplemental mandrels. As zero degree construction locks the supplemental mandrels in place radially, it is undesirable where varying the pitch of the supplemental mandrel along the main process mandrel is required.

Additionally, use of the horn gears as a pass-through for the supplemental mandrels limits the number of supplemental mandrels that may be applied to the main process mandrel. For example, a sixteen carrier braider can apply up to eight mandrels, a twenty-four carrier braider can only have up to twelve mandrels. In contrast, use of holes in the nose cone allows any number of mandrels to be passed through to the main process mandrel.

In some embodiments, the supplemental mandrels may be applied to the main process mandrel without the benefit of a second, outer layer of braid wire. Instead, the supplemental mandrels may be applied without braid wire. In those embodiments, the bonded/fused polymer jacket may hold the mandrels, and thus lumens in place. Alternatively, in some embodiments, the mandrels may be held in place using a casting around the braided composite. Since the outer braid layer is absent from the manufacturing endoscopic device, the diameter and circumference of the device cross-section is reduced. Alternatively, the supplemental mandrels may be held in place by sleeving a polymer jacket over the process mandrel. In some embodiments, the casting is the same material as the exterior material for the endoscopic device.

In some embodiments, the supplemental mandrels may be braided onto the main process mandrel much like the braid wire. For example, in some embodiments, the supplemental mandrels may be braided using the even numbered horn gears, while held in place by braid wire braided using the odd numbered horn gears. In this way, the supplemental mandrels, and thus the lumens may be woven into the walls of the central lumen. As an added benefit, embodiments manufactured using this means also tend to have lower circumferential area.

Alternatively, in some embodiments, the helixed lumen structures may be manufactured using extruded molds. These molds may generate the helixed lumen structures to create a jacket from PTFE, pebax, polyurethane, and nylon. In some embodiments, the extruded structures may be formed using a mold around a braided mandrel.

Construction of sheath 900 from FIG. 9 and flexible endoscope 1000 from FIG. 10 are substantially the same. Thus, one of skill in the art would understanding that the same principles apply to both tools.

Figure 16:
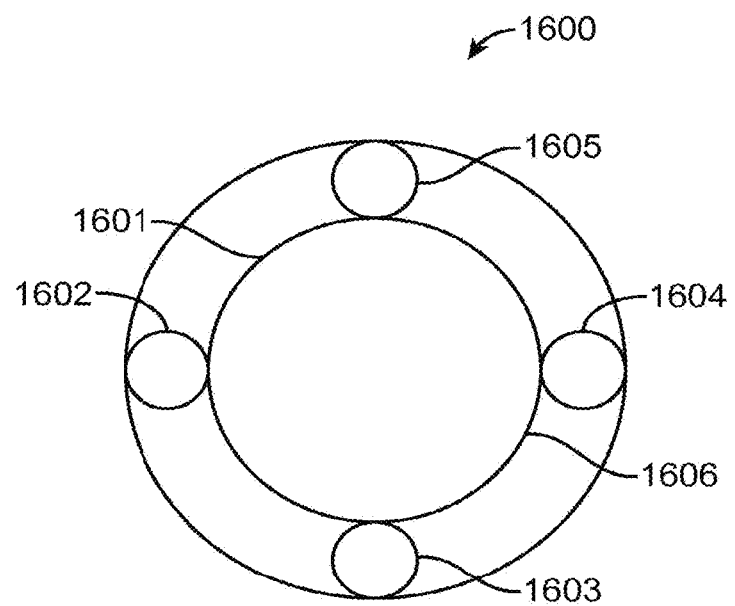
FIG. 16 illustrates a cross-sectional view of a flexible endoscopic device where the pull lumens are arranged symmetrically around the circumference of the device, in accordance with an embodiment of the present invention.

In some embodiments, the helixed lumens may be positioned to be equidistant from each other. FIG. 16 illustrates a cross-sectional view of a flexible endoscopic device where the pull lumens are arranged symmetrically around the circumference of the device, in accordance with an embodiment of the present invention. As shown in FIG. 16, device 1600 has a central working channel 1601 and pull lumens (1602, 1603, 1604, and 1605) spaced symmetrically around the working channel 1601 and within the outer jacket 1606.

In some embodiments, though helixed, the lumens and pull wires may not be distributed evenly or equidistant from each other around the circumference of the sheath and/or flexible endoscope. In some applications, grouping all of the lumens and pull wires onto the same side or hemispheric region (e.g., top vs. bottom hemisphere) of the sheath and endoscope allows for a smaller outer diameter. This may be desirable for certain applications and procedures.

Figure 17A:
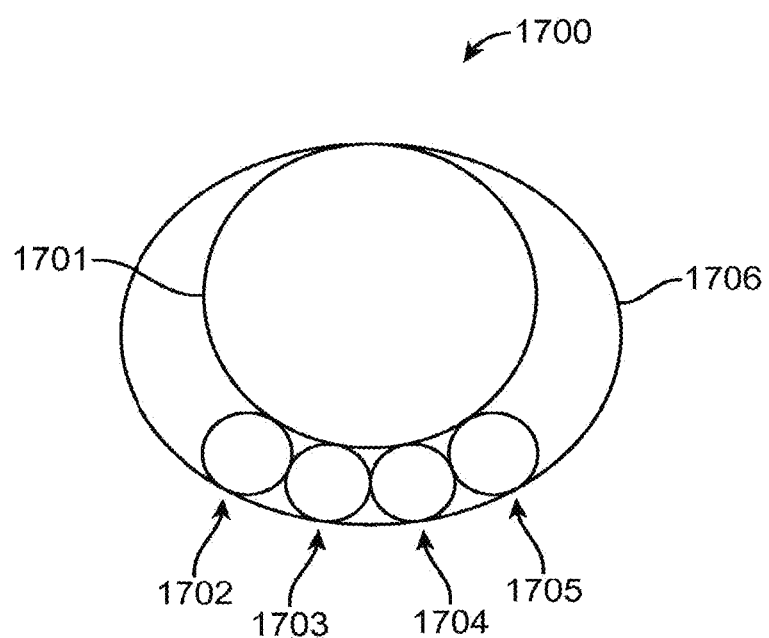
FIG. 17A illustrates a cross-sectional view of a flexible endoscopic device where the pull lumens are not arranged symmetrically around the circumference of the device, in accordance with an embodiment of the present invention.

FIG. 17A illustrates a cross-sectional view of a flexible endoscopic device where the pull lumens are not arranged symmetrically around the circumference of the device, in accordance with an embodiment of the present invention. Similar to device 1600 of FIG. 16, device 1700 has a working channel 1701, pull lumens 1702, 1703, 1704, and 1705, and an outer jacket 1706. In some embodiments, the working channel may be created by a small hollow tube ("hypo tube") created from a flexible metal alloy, such as nitinol.

Rather than arranged equidistant from each other, however, pull lumens 1702, 1703, 1704, and 1705 are grouped together to reduce the outside diameter of the device, as shown by the circumference of the outer jacket 1706. Even though the pull lumens are not equidistant from each other around the circumference of the working channel 1701, helixing the pull lumens in the arrangement shown in device 1700 still exhibits the advantages of helixing, e.g., avoiding muscling or curve alignment phenomena. Although the pull lumens of device 1700 are arranged adjacent to each other around working channel 1701, other embodiments may be arranged in a different pattern, such as spaced out within same hemisphere or clustered together. The jacket 1706 may be created from plastic or any other material that may be stretched, bonded or melted during the manufacture of device 1700.

Figure 17B:
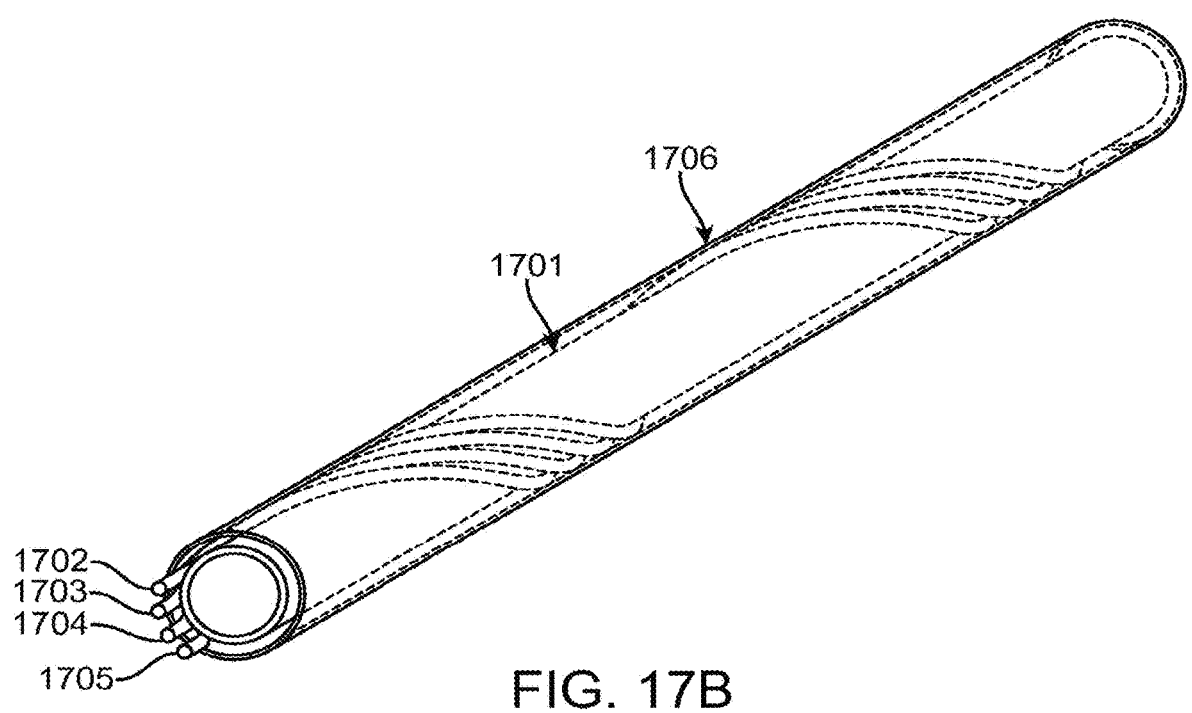
FIG. 17B illustrates an isometric view of the flexible endoscopic device in FIG. 17A, in accordance with an embodiment of the present invention.

FIG. 17B illustrates an isometric view of the flexible endoscopic device 1700 disclosed in FIG. 17A, in accordance with an embodiment of the present invention. As shown in the isometric view of FIG. 18, pull lumens 1702, 1703, 1704, and 1705 helix around the working channel 1701. In some embodiments, the pitch of the helixed pull lumens may be varied in order to obtain desired properties, such as stiffness and bending flexibility, from device 1700.

Figure 18:
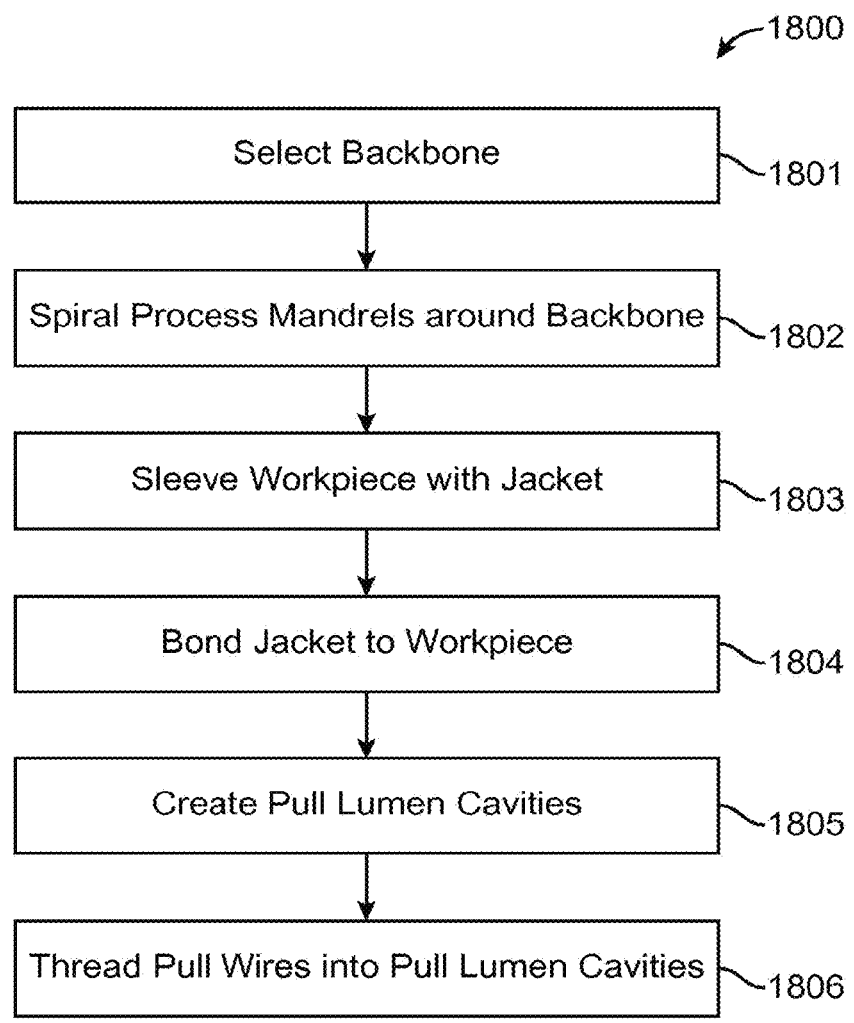
FIG. 18 illustrates a flow diagram for a method for manufacturing the flexible endoscopic device in FIG. 17A-17B, in accordance with an embodiment of the present invention.

FIG. 18 illustrates a flow diagram for a method for manufacturing device 1700, in accordance with an embodiment of the present invention. As shown in step 1801, the manufacturing process 1800 begins with selecting a backbone for the workpiece. In some embodiments, the backbone may be a hollow tube, such as a hypodermic "hypo" tube formed from nitinol alloy. A person skilled in the art would recognize that a hypotube may be a small, micro or nano radius tube as small as 0.005" in outside diameter. A person skilled in the art would recognize that tube materials may be preferred since tubular structures simultaneously exhibit axial stiffness and low bending stiffness. The use of a stiff or semi-stiff backbone, such a nitinol alloy, would also increase axial stiffness as well as hoop strength. Additionally, the tube provides for a working channel through which useful tools and cables may be inserted, such as optics, aspiration, irrigation, and controls. In an embodiment where a central working channel is not required, the backbone may be a solid rod, such as for use as an articulable guidewire.

Following the selection of a backbone, in step 1802, process mandrels (one or more) may be spiraled around the backbone at the desired pitch. In some embodiments, the process mandrels may be coated with polytetrafluoroethylene (PTFE) for easy removal during step 1805. The pitch of the spiraled mandrels may fixed or dynamic, allowing for the different bending and stiffness properties depending on the application. The lower the pitch, i.e., more longitudinally parallel to the neutral axis of the backbone, the lower the axial compression under tension, while also exhibiting increased muscling and curve alignment phenomena. Higher pitch spiraling generally exhibits reduced muscling and curve alignment phenomena at the cost of increased axial compression under tension.

In step 1803, the resulting workpiece, comprising of a backbone and at least one spiraled mandrel, may be sheathed or covered in a "jacket". In some embodiments, the jacket is a simple extruded tube or sheath. Selection of the means of the sheathing is critical; as sheathing may inadvertently alter the pitch of the process mandrels around the backbone. In some embodiments, the "sheathing" process may be accomplished by casting, deposition, overextrusion, or any other means that would be known in the art.

In step 1804, if not already bonded from the sheathing process, the jacket may be bonded to the workpiece. This may involve melting, molding or bonding to the workpiece using any number of processes known to one skilled in the art. Once bonded, the jacket will hold the process mandrels in place.

In step 1805, once the bonding process is complete, the spiraled process mandrels may be removed to create helixed pull lumen cavities that run longitudinally along the length of the workpiece. In step 1806, following removal of the mandrels, the pull wires may be threaded into the remaining cavities. In operation, the pull wires may then be used to facilitate pull wires for articulating the endoscopic device.

As method 1800 does not make use of braiding, it provides for the construction of workpieces and devices with relatively small outer diameters, which may be appropriate for reaching areas requiring small instruments, e.g., microsurgical applications. While the method of manufacture previously discussed may be applied to devices of varying sizes and outer diameters, the preferred embodiments generally have an outer diameter of less than 2 mm.

Integration of the resulting workpiece into an endoscopic device may be accomplished by melting, molding, bonding, and casting the workpiece jacket to the outer jacket of other components, such as a flexure or tool tip. In some embodiments, the backbone may include structure for an adjoining microsurgical flexure tool, such as ribbing for an increased bend radius and longitudinally-aligned cavities for tools and control wires.

Figure 19:
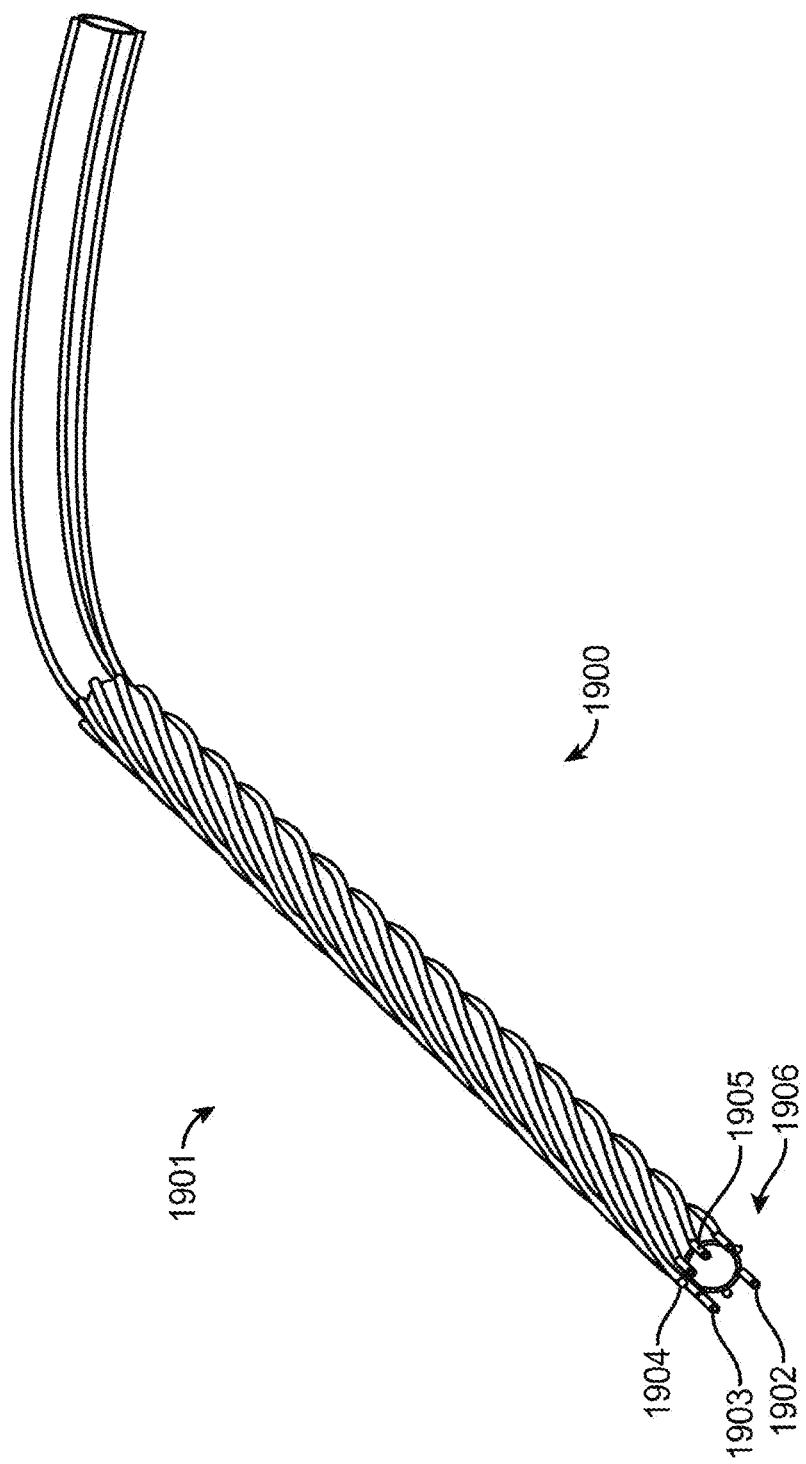
FIG. 19 illustrates an isometric view of a flexible endoscopic device with a nitinol hypotube backbone and a helixed payload lumen, in accordance with an embodiment of the present invention.

FIG. 19 illustrates an isometric view of a flexible endoscopic device with a hypotube backbone and helixed lumens, in accordance with an embodiment of the present invention. As shown in isometric view 1900, endoscopic device 1901 may be constructed from a solid hypotube backbone 1902, preferentially constructed from a semi-rigid material, such as nitinol alloy. Different embodiments have been shown to work with different alloys. In addition, various sizes of hypotubes may be employed depending on the desired characteristics of the endoscopic device 1901. In some embodiments, the inner diameter of the hypotubes may range in size from 0.015" to 0.050" with wall thickness ranging from 0.001" to 0.005".

Lumens 1902, 1903, 1904, 1905, and 1906 may be spiraled around the nitinol backbone. In some embodiments, a subset of lumens 1902, 1903, 1904, 1905, and 1906 may be sized to convey pull wires down the length of the endoscopic device 1901. As discussed earlier, pull wires may be used to apply compressive force along the endoscopic device to induce articulation at a distal location.

In some embodiments, a subset of lumens 1902, 1903, 1904, 1905, and 1906 may be used as payload lumens to convey laser fibers, mechanical tools, irrigation, aspiration, or other payloads that may be useful for diagnostic or therapeutic applications. Use of spiraled payload lumens potentially frees up the central working channel for other (often larger) payloads. Payload lumens that are spiraled around the hypotube backbone also balance the compressive and extension forces on a payload that results for navigation through tortuous pathways. In contrast, those forces may affect, degrade or damage the payload when the payload lumens run longitudinally straight along the backbone. In some embodiments, the central working channel may convey a concentrically aligned endoscopic device that may be used for extension or retraction.

FIG. 20A illustrates an isometric view of a flexible endoscopic device with a hypotube backbone and non-uniformly spaced helixed lumens, in accordance with an embodiment of the present invention. Endoscopic device 2000 may be similarly constructed around a hypotube backbone 2001 that may use a nitinol alloy. Unlike endoscopic device 1901 from FIG. 19, lumens 2002, 2003, 2004, 2005, 2006, 2007, 2008, and 2009 may arranged around the backbone 2001 without uniform spacing. As with device 1700 from FIG. 17, lumens 2002, 2003, 2004, 2005, 2006, 2007, 2008, and 2009 may be arranged to reduce the outside diameter of device 2000. As with device 1901 from FIG. 19, these lumens may be configured to convey a combination of pull wires, laser fibers, mechanical tools, irrigation, aspiration, or other payloads that may be useful for diagnostic or therapeutic applications at a distal location.

Figure 20B:
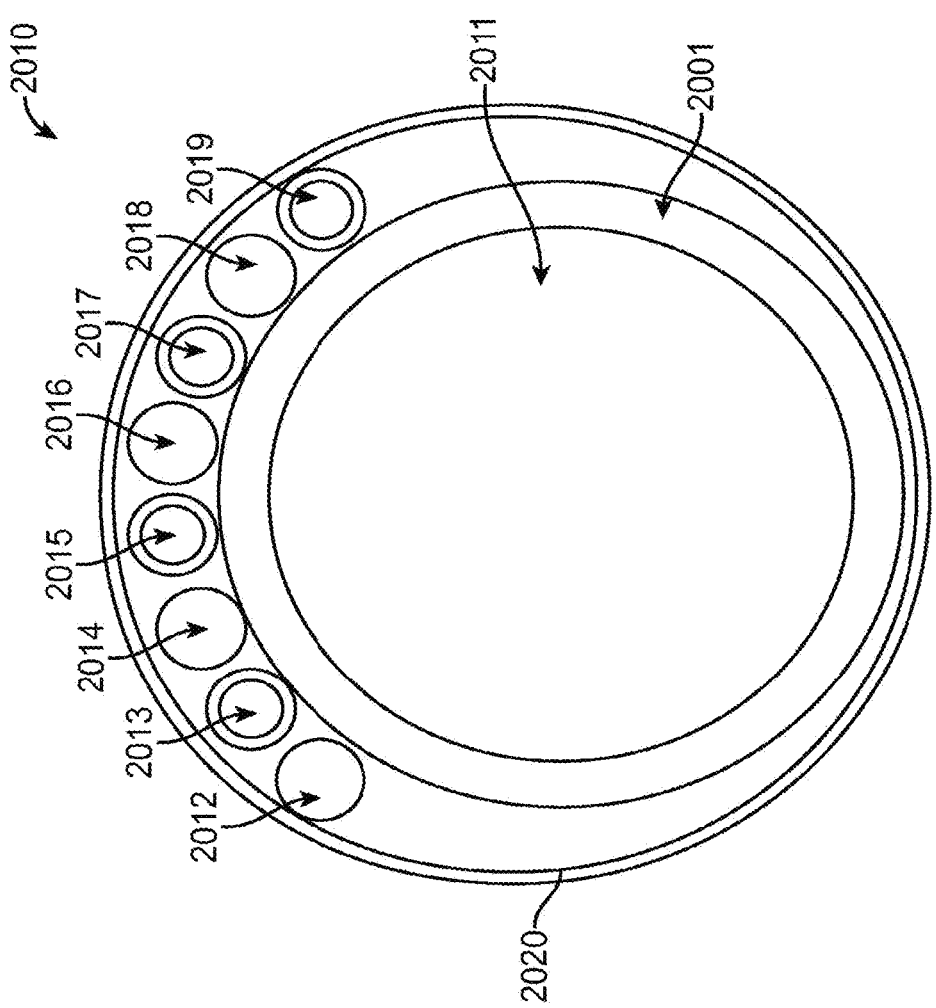
FIG. 20B illustrates a cross-sectional view of the distal end of endoscopic device 2000 from FIG. 20A.

FIG. 20B illustrates a cross-sectional view of the distal end of endoscopic device 2000 from FIG. 20A. As shown in distal view 2010, the distal end of endoscopic device 2001 provides access to a working channel 2011, and access ports to lumens 2002, 2003, 2004, 2005, 2006, 2007, 2008, and 2009 as shown by 2012, 2013, 2014, 2015, 2016, 2017, 2018 and 2019. In some embodiments, the access ports 2012, 2014, 2016, and 2018 may be inaccessible since they serve as lumens for pull wires. In those embodiments, access ports 2012, 2014, 2016, and 2018 may be sealed due to anchoring of their related pull wires. In some embodiments, the lumens may be held in place using an exterior jacket 2020.

As with other embodiments that are constructed using a hypotube backbone, endoscopic devices 1901 and 2000 may be constructed using the manufacturing process 1800 from FIG. 18.

Figure 21:
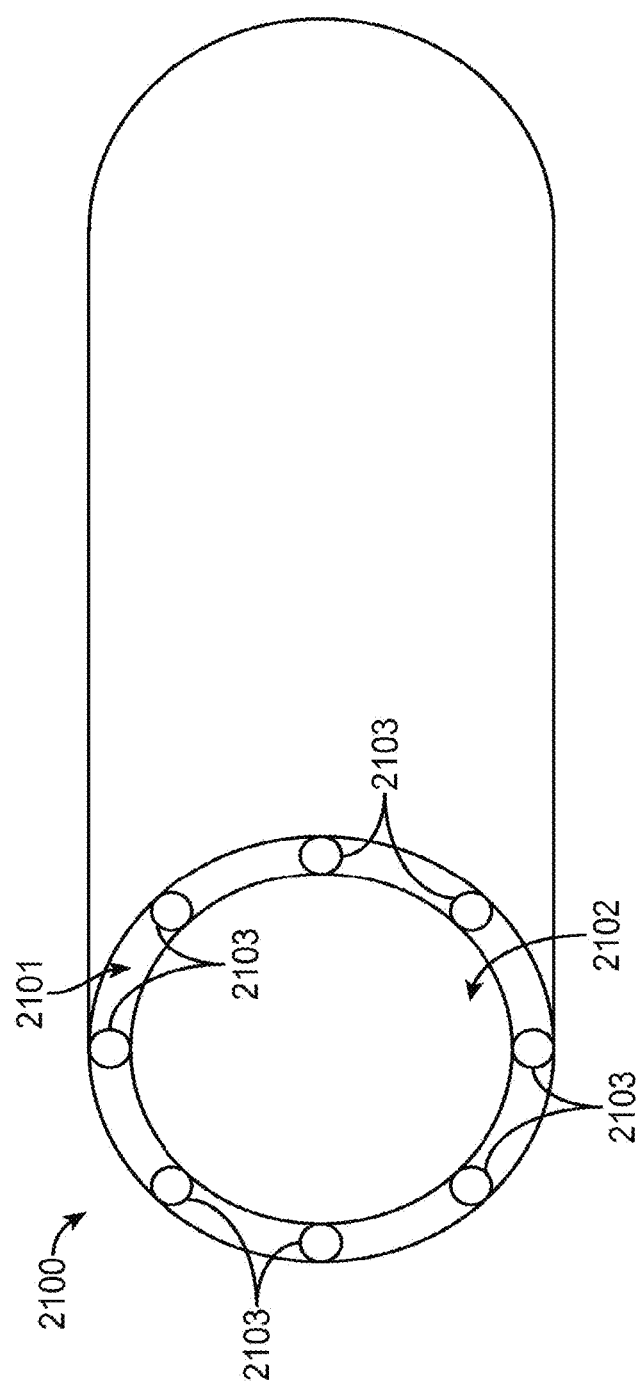
FIG. 21 illustrates an endoscopic device with helixed lumens that was created using extrusion-based manufacturing techniques, in accordance with an embodiment of the present invention.

FIG. 21 illustrates an endoscopic device with helixed lumens that was created using extrusion-based manufacturing techniques, in accordance with an embodiment of the present invention. As shown in FIG. 21, an endoscopic device 2100 may be constructed by extruding a wall 2101 formed from thermoplastic material around a working channel 2102. In some embodiments, the endoscopic device may have multiple working channels.

In certain embodiments, the wall 2101 may be formed from a variety of thermoplastic material, including but not limited to pebax, nylon, or polyurethane. In certain embodiments, the wall thickness may be as thin as 0.010" or as thick as 0.030". In certain embodiments, the outer diameter of such a device 2100 may range from 0.060" to 0.200". A series of lumens 2103 may be built into the wall 2101 for purposes of conveying actuation tendons (such as pull wires), tools and means for irrigation, aspiration, illumination, and image capture. Much like the embodiments disclosed earlier, lumens 2103 may also be spiraled or helixed along a certain portion of the length of the device where muscling and curve alignment phenomena are intended to be minimized. As in other embodiments, the extent and pitch of the spiral/helix may be predetermined and designed with specific applications and properties in mind.

Figure 22:
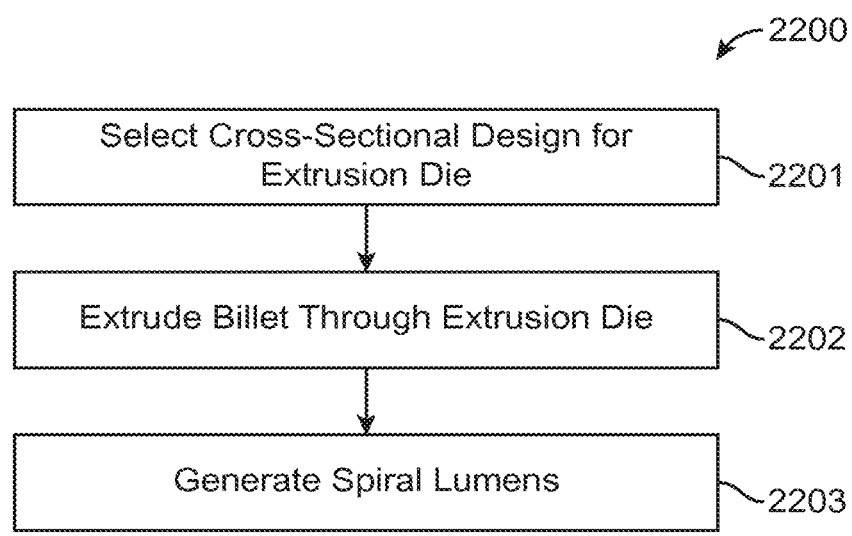
FIG. 22 illustrates a flow chart for a method of manufacturing an endoscopic device with spiraled lumens, such as endoscopic device 2100, using direct extrusion-based manufacturing techniques, in accordance with an embodiment of the present invention.

FIG. 22 illustrates a flow chart for a method of manufacturing an endoscopic device with spiraled lumens, such as endoscopic device 2100, using direct extrusion-based manufacturing techniques, in accordance with an embodiment of the present invention. In step 2201 of process 2200, a manufacturer may first select the device and cross-sectional profile of the desired workpiece. The selected cross-sectional profile may vary depending on the application and intended use of the resulting endoscope. In some embodiments, a thicker wall may be desirable to improved stiffness. In some embodiments, a thinner wall may be desirable to improve bendability. Additionally, a thinner wall may be desirable to reduce the outside diameter in order to fit in smaller anatomical lumens and hard-to-reach areas of the patient's anatomy.

When selecting the desired cross-sectional profile, the manufacturer may also vary the size of the desired working channel and the size and number of lumens. Altering the size of the working channel allow a larger channel or increased wall thickness for more stiffness. In some embodiments, only a few lumens may be necessary for the intended application. In some embodiments, more than eight lumens may be desirable, often at the cost of stiffness. Having selected the desired cross-sectional profile, the cross-sectional profile may be used to create an extrusion die.

In step 2202, the extrusion may begin using the selected die shape from the cross-sectional profile in 2201. Typically, the billet material may be a thermoplastic, such as pebax, nylon, or polyurethane. The extrusion length may be determined based on the amount of the billet material pushed through the die.

In step 2203, the spiral lumens may be generated. There are several methods of generating the desired helixed configuration. In one method, the extrusion may be rotated as it is being made, i.e., as the billet is pushed through the die, the extruded material may be rotated as it exits the die. In another method, the die itself may be rotated relative to the billet in order to generate the desired spiraling. In either method, the rotation may be customized, allowing for a variety of helical and spiral pitches based on the desired properties of the endoscopic device. For example, a more aggressive pitch may require faster rotation of the die and/or extruded material. A gentler pitch may be created using a slower rotation.

Alternatively, the spiraling may be generated after the completion of the extrusion process. In certain embodiments, the extrusion may be subsequently heated and twisted in order to generate the desired properties. In some circumstances, this may involve heating the extrusion to its glass-transition temperature in order to make the material pliable. After twisting the extrusion to obtain the desired pitch, the extrusion may be quickly cooled to lock the pitch of the spiraled lumens in place.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. An endoscopic method comprising:
providing an elongated medical device comprising:
a hypotube backbone running along a length of the elongated medical device and forming a central working channel; and
a plurality of spiral lumens spiraled around the hypotube backbone along the length of the elongated medical device, the plurality of spiral lumens comprising:
a first spiral lumen having an articulation pull wire disposed therein; and
a second spiral lumen rotationally-offset from first spiral lumen with respect to an axis of the hypotube backbone, the second spiral lumen forming a distally-open working channel;
directing the elongate medical device into an anatomical lumen; and
positioning the elongate medical device at a desired operative region through the anatomical lumen.

2. The method of claim 1, wherein the hypotube backbone is formed from a nitinol alloy.

3. The method of claim 2, wherein the hypotube backbone is configured to provide axial stiffness along the length of the elongate medical device.

4. The method of claim 1, wherein the hypotube backbone provides a central lumen that runs along the length of the device.

5. The method of claim 4, wherein the central lumen is configured to deliver a central payload from a proximal end of the elongate medical device to a distal opening of the central lumen.

6. The method of claim 5, wherein the central payload comprises at least one of a laser fiber, a surgical tool, an imaging means, an irrigation means, or an aspiration means.

7. The method of claim 1, wherein the first spiral lumen is closed at a distal end thereof.

8. The method of claim 7, wherein the second spiral lumen is configured to receive therein at least one of a laser fiber, a surgical tool, an imaging means, an irrigation means, or an aspiration means.

9. The method of claim 1, wherein a jacket surrounds the hypotube backbone and the plurality of spiral lumens.

10. An endoscopic method comprising:
providing an elongated medical device comprising:
a hypotube backbone running along a length of the elongated medical device;
a spiral lumen spiraled around the hypotube backbone along the length of the elongated medical device; and
a pull wire extending through the spiral lumen and configured to induce articulation of the elongated medical device;
directing the device into an anatomical lumen; and
positioning the elongated medical device at a desired operative region through the anatomical lumen;
wherein the spiral lumen comprises a variable pitch section in which a pitch of the spiral lumen spiral spiraled around the backbone varies.

11. The method of claim 1, wherein the plurality of spiral lumens comprises four or more spiral lumens.

12. The method of claim 11, wherein the four or more spiral lumens are uniformly spaced about a circumference of the hypotube backbone.

13. The method of claim 11, wherein the four or more spiral lumens are non-uniformly spaced about a circumference of the hypotube backbone.

14. The method of claim 11, wherein the four or more spiral lumens comprises:
a first set of two or more distally-closed spiral pull wire lumens that includes the first spiral lumen; and
a second set of two or more distally-open spiral payload lumens that includes the second spiral lumen.

15. The method of claim 14, wherein lumens of the first set of pull wire lumens and lumens of the second set of payload lumens are alternated about a circumference of the hypotube backbone.

16. An endoscopic method comprising:
providing an elongated medical device comprising:
a hypotube backbone running along a length of the elongated medical device and forming a central working channel; and
a plurality of spiral lumens spiraled around the hypotube backbone along the length of the elongated medical device, the plurality of spiral lumens being asymmetrically arranged around a circumference of the hypotube backbone;
directing the device into an anatomical lumen; and
positioning the device at a desired operative region through the anatomical lumen.

17. The method of claim 16, wherein, at a distal end of the plurality of spiral lumens, the plurality of spiral lumens are grouped together on a single diametrical side of the elongated medical device.

18. The method of claim 16, wherein the plurality of spiral lumens comprises four or more spiral lumens.

19. The method of claim 18, wherein the four or more spiral lumens comprise alternating pull wire and payload lumens.

\* \* \* \* \*